United States Patent
Long et al.

(10) Patent No.: US 7,691,878 B2
(45) Date of Patent: Apr. 6, 2010

(54) HETEROARYLALKYL-8-AZABICYCLO[3.2.1]OCTANE COMPOUNDS AS MU OPIOID RECEPTOR ANTAGONISTS

(75) Inventors: Daniel D. Long, San Francisco, CA (US); Lan Jiang, Foster City, CA (US); Daisuke Roland Saito, Burlingame, CA (US); Priscilla Van Dyke, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 12/229,737

(22) Filed: Aug. 26, 2008

(65) Prior Publication Data

US 2009/0062334 A1   Mar. 5, 2009

Related U.S. Application Data

(60) Provisional application No. 60/966,317, filed on Aug. 27, 2007.

(51) Int. Cl.
A61K 31/46 (2006.01)
C07D 221/02 (2006.01)
C12Q 1/02 (2006.01)
A61P 1/00 (2006.01)

(52) U.S. Cl. .................. 514/304; 546/125; 435/29
(58) Field of Classification Search .......... 514/304; 546/125; 435/29
See application file for complete search history.

(56) References Cited

U.S. PATENT DOCUMENTS

| | | |
|---|---|---|
| 5,159,081 A | 10/1992 | Cantrell et al. |
| 6,313,312 B1 | 11/2001 | Banks et al. |
| 6,469,030 B2 | 10/2002 | Farrar et al. |
| 6,479,516 B1 | 11/2002 | Gibson et al. |
| 6,593,348 B2 | 7/2003 | Carroll et al. |
| 6,610,711 B2 | 8/2003 | Armer et al. |
| 7,049,335 B2 | 5/2006 | McHardy et al. |
| 7,056,930 B2 | 6/2006 | Coe et al. |
| 7,087,749 B2 | 8/2006 | Dolle et al. |
| 7,241,887 B2 | 7/2007 | Coe et al. |
| 7,375,234 B2 | 5/2008 | Sharpless et al. |
| 2002/0025948 A1 | 2/2002 | Banks et al. |
| 2003/0181447 A1 | 9/2003 | Boyd et al. |
| 2004/0186135 A1 | 9/2004 | Dolle et al. |
| 2004/0204453 A1 | 10/2004 | McHardy et al. |
| 2004/0254190 A1 | 12/2004 | Liras |
| 2004/0254218 A1 | 12/2004 | Le Bourdonnec et al. |
| 2007/0105863 A1 | 5/2007 | Dolle et al. |
| 2007/0219278 A1* | 9/2007 | Long et al. .......... 514/741 |
| 2008/0207676 A1 | 8/2008 | Dalziel et al. |
| 2009/0023934 A1 | 1/2009 | Colson et al. |
| 2009/0062332 A1 | 3/2009 | Saito et al. |
| 2009/0062333 A1 | 3/2009 | Saito et al. |
| 2009/0062335 A1 | 3/2009 | Long et al. |

OTHER PUBLICATIONS

Le Bourdonnec et al., "*trans*-3,4-Dimethyl-4-(3-carboxamidophenyl)piperidines: A Novel Class of μ-Selective Opioid Antagonists", Bioorganic & Medicinal Chemistry Letters, vol. 13 pp. 4459-4462 (2003).
Le Bourdonnec et al., "Elucidation of the Bioactive Conformation of the *N*-Substituted *trans*-3,4-Dimethyl-4-(3-hydroxyphenyl)piperidine Class of μ-Opioid Receptor Antagonists", Journal of Medicinal Chemistry, vol. 49, pp. 7278-7289 (2006).
Le Bourdonnec et al., "Synthesis and Pharmacological Evaluation of Novel Octahydro-1*H*-pyrido[1,2-a]pyrazine as μ-Opioid Receptor Antagonists", Journal of Medicinal Chemistry, vol. 49, pp. 7290-7306 (2006).
Diaz et al., "SAR and Biological Evaluation of Novel *trans*-3,4-dimethyl-4-arylpiperidine Derivatives as Opioid Antagonists", Bioorganic & Medicinal Chemistry Letters, vol. 15 pp. 3844-3848 (2005).
Lu et al., "Substituted Bridged Phenyl Piperidines: Orally Active Growth Hormone Secretagogues", Bioorganic & Medicinal Chemistry Letters, 13, pp. 1817-1820 (2003).
International Search Report for PCT/US2008/010091.
Rostovtsev et al., "A Stepwise Huisgen Cycloaddition Process: Copper(I)-Catalyzed Regioselective "Ligation" of Azides and Terminal Alkynes", Angew. Chem. Int. Ed., 41(14), pp. 2596-2599 (2002).
Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides", J. Org. Chem., 67, pp. 3057-3064 (2002).

\* cited by examiner

*Primary Examiner*—D. Margaret Seaman
*Assistant Examiner*—Niloofar Rahmani
(74) *Attorney, Agent, or Firm*—Jeffrey A. Hagenah; Roberta P. Saxon

(57) ABSTRACT

The invention provides heteroarylene substituted 8-azabicyclo[3.2.1]octane compounds of formula (I):

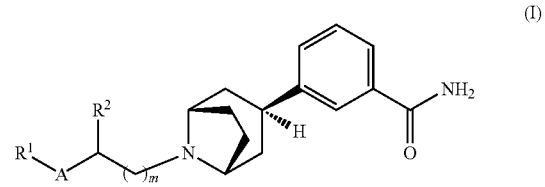

(I)

wherein $R^1$, $R^2$, A, and m are defined in the specification, or a pharmaceutically-acceptable salt thereof, that are antagonists at the mu opioid receptor. The invention also provides pharmaceutical compositions comprising such compounds, methods of using such compounds to treat conditions associated with mu opioid receptor activity, and processes and intermediates useful for preparing such compounds.

19 Claims, No Drawings

HETEROARYLALKYL-8-AZABICYCLO[3.2.1]OCTANE COMPOUNDS AS MU OPIOID RECEPTOR ANTAGONISTS

CROSS-REFERENCE TO RELATED APPLICATIONS

This application claims the benefit of U.S. Provisional Application No. 60/966,317, filed on Aug. 27, 2007, the disclosure of which is incorporated herein by reference in its entirety.

BACKGROUND OF THE INVENTION

1. Field of the Invention

The invention is directed to 8-azabicyclo[3.2.1]octane compounds which are useful as mu opioid receptor antagonists. The invention is also directed to pharmaceutical compositions comprising such compounds, methods of using such compounds for treating or ameliorating medical conditions mediated by mu opioid receptor activity, and processes and intermediates useful for preparing such compounds.

2. State of the Art

It is now generally understood that endogenous opioids play a complex role in gastrointestinal physiology. Opioid receptors are expressed throughout the body, both in the central nervous system and in peripheral regions including the gastrointestinal (GI) tract.

Compounds which function as agonists at opioid receptors, of which morphine is a prototypical example, are the mainstays of analgesic therapy for the treatment of moderate to severe pain. Unfortunately, use of opioid analgesics is often associated with adverse effects on the GI tract, collectively termed opioid-induced bowel dysfunction (OBD). OBD includes symptoms such as constipation, decreased gastric emptying, abdominal pain and discomfort, bloating, nausea, and gastroesophageal reflux. Both central and peripheral opioid receptors are likely involved in the slowdown of gastrointestinal transit after opioid use. However, evidence suggests that peripheral opioid receptors in the GI tract are primarily responsible for the adverse effects of opioids on GI function.

Since the side effects of opioids are predominantly mediated by peripheral receptors, whereas the analgesia is central in origin, a peripherally selective antagonist can potentially block undesirable GI-related side effects without interfering with the beneficial central effects of analgesia or precipitating central nervous system withdrawal symptoms.

Of the three major opioid receptor subtypes, denoted mu, delta, and kappa, most clinically-used opioid analgesics are thought to act via mu opioid receptor activation to exert analgesia and to alter GI motility. Accordingly, peripherally selective mu opioid antagonists are expected to be useful for treating opioid-induced bowel dysfunction. Preferred agents will demonstrate significant binding to mu opioid receptors in vitro and be active in vivo in GI animal models.

Postoperative ileus (POI) is a disorder of reduced motility of the GI tract that occurs after abdominal or other surgery. The symptoms of POI are similar to those of OBD. Furthermore, since surgical patients are often treated during and after surgery with opioid analgesics, the duration of POI may be compounded by the reduced GI motility associated with opioid use. Mu opioid antagonists useful for treating OBD are therefore also expected to be beneficial in the treatment of POI.

SUMMARY OF THE INVENTION

The invention provides novel compounds that possess mu opioid receptor antagonist activity.

Accordingly, the invention provides a compound of formula (I):

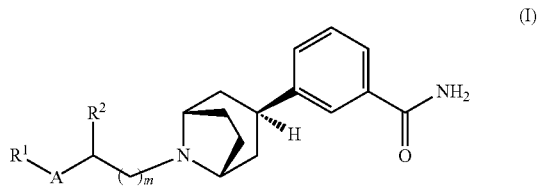

wherein:

A is a five-membered heteroarylene ring containing one, two, three, or four heteroatoms selected from nitrogen, oxygen and sulfur, wherein not more than one of the heteroatoms is oxygen or sulfur;

$R^1$ is selected from —C(O)O$R^a$, —C(O)N$R^b R^c$, $C_{2-6}$alkenyl, $C_{1-6}$ alkyl, $C_{3-12}$cycloalkyl, and phenyl, wherein $C_{1-6}$alkyl is optionally substituted with one or two $R^3$, $C_{3-12}$cycloalkyl is optionally substituted with one or two halo or with —O$R^a$ or —N$R^b R^c$, and phenyl is optionally substituted with one or two halo or with —O$R^a$, —N$R^b R^c$, or $C_{1-4}$alkyl, wherein $C_{1-4}$alkyl is optionally substituted with —O$R^a$;

$R^2$ is hydrogen or phenyl;

$R^3$ is selected from —C(O)O$R^a$, —C(O)N$R^d R^e$, —O$R^f$, —CN, $C_{3-6}$cycloalkyl, phenyl, and naphthyl, wherein $C_{3-6}$cycloalkyl is optionally substituted with one or two halo or with —O$R^a$, and phenyl is optionally substituted with one or two halo or with —CN;

$R^a$, $R^b$, $R^c$, and $R^d$ are each independently hydrogen or $C_{1-3}$alkyl;

$R^e$ is hydrogen or $C_{1-3}$alkyl, optionally substituted with $C_{3-6}$cycloalkyl, —O$R^a$, phenyl, pyridyl, or 4-phenylpiperazinyl; or $R^d$ and $R^e$ taken together with the nitrogen atom to which they are attached form piperidinyl;

$R^f$ is hydrogen, $C_{1-3}$alkyl, or phenyl;

$R^g$ is hydrogen or $C_{1-3}$alkyl, optionally substituted with phenyl; and m is 0, 1, or 2;

provided that when m is 0, $R^2$ is H;

or a pharmaceutically-acceptable salt thereof.

The invention also provides a pharmaceutical composition comprising a compound of the invention and a pharmaceutically-acceptable carrier.

The invention also provides a method of treating a disease or condition ameliorated by treatment with a mu opioid receptor antagonist, e.g. a disorder of reduced motility of the gastrointestinal tract such as opioid-induced bowel dysfunction and post-operative ileus, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt thereof, as a research tool for studying a biological system or sample or for discovering new compounds having mu opioid receptor activity, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition ameliorated by treatment with a mu opioid receptor antagonist, e.g. a disorder of reduced motility of the gastrointestinal tract, in a mammal.

DETAILED DESCRIPTION OF THE INVENTION

The invention provides 8-azabicyclo[3.2.1]octane mu opioid receptor antagonists of formula (I), or pharmaceutically-acceptable salts thereof. The following substituents and values are intended to provide representative examples of various aspects of this invention. These representative values are intended to further define such aspects and are not intended to exclude other values or limit the scope of the invention.

In a specific aspect, $R^1$ is selected from —C(O)OR$^a$, —C(O)NR$^b$R$^c$, $C_{2-6}$alkenyl, $C_{1-6}$alkyl, $C_{3-12}$cycloalkyl, and phenyl, wherein $C_{1-6}$alkyl is optionally substituted with one or two $R^3$, $C_{3-12}$cycloalkyl is optionally substituted with one or two halo or with —OR$^a$ or —NR$^b$R$^c$, and phenyl is optionally substituted with one or two halo or with —OR$^a$, —NR$^b$R$^c$, or $C_{1-4}$alkyl, wherein $C_{1-4}$alkyl is optionally substituted with —OR$^a$.

In another specific aspect, $R^1$ is selected from $C_{1-6}$alkyl, $C_{3-6}$cycloalkyl, and phenyl, wherein $C_{1-6}$alkyl is optionally substituted with one or two $R^3$, $C_{3-6}$cycloalkyl is optionally substituted with one or two halo or with —OR$^a$ or —NR$^b$R$^c$, and phenyl is optionally substituted with one or two halo or with —OR$^a$, —NR$^b$R$^c$, or $C_{1-4}$alkyl, wherein $C_{1-4}$alkyl is optionally substituted with —OR$^a$.

In other specific aspects, $R^1$ is $C_{1-6}$alkyl, wherein $C_{1-6}$alkyl is optionally substituted with one $R^3$, or $R^1$ is $C_{1-6}$alkyl.

In yet another specific aspect, $R^1$ is cyclopentyl, cyclohexyl or phenyl, wherein cyclohexyl and phenyl are each optionally substituted with one or two fluoro, or with —OH or —NH$_2$. Representative $R^1$ groups within this aspect include, but are not limited to cyclopentyl, cyclohexyl, phenyl, 4,4-difluorocyclohexyl, 4-fluorocyclohexyl, 2,4-difluorophenyl, and the like.

In yet another aspect, $R^1$ is selected from $C_{1-6}$alkyl, cyclopentyl, cyclohexyl, and phenyl, wherein $C_{1-6}$alkyl is optionally substituted with one $R^3$, and cyclohexyl and phenyl are each optionally substituted with one or two fluoro.

In yet another aspect, $R^1$ is selected from $C_{1-6}$alkyl, cyclopentyl, cyclohexyl, and phenyl, wherein cyclohexyl and phenyl are each optionally substituted with one or two fluoro.

In a still further specific aspect, $R^1$ is selected from —C(O)OR$^a$, —C(O)NR$^b$R$^c$, and $C_{1-3}$alkyl substituted with one $R^3$.

In a specific aspect, A is a five-membered heteroarylene ring containing one, two, three, or four heteroatoms selected from nitrogen, oxygen and sulfur, wherein not more than one of the heteroatoms is oxygen or sulfur.

In another specific aspect, A is selected from triazolenyl, imidazolenyl, oxadiazolenyl, tetrazolenyl, pyrrolenyl, furanenyl, and thiofuranenyl.

In a specific aspect, A is selected from triazolenyl, imidazolenyl, and oxadiazolenyl. In another specific aspect, A is triazolenyl.

In a specific aspect, $R^1$-A- is selected from a moiety of formula (a), (b), (c), (d) and (e):

(a)

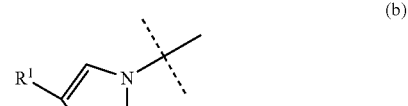

(b)

(c)

(d)

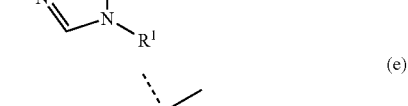

(e)

In another specific aspect, $R^1$-A- is a moiety of formula (a) or (b).

In a specific aspect, $R^2$ is hydrogen or phenyl. In other specific aspects, $R^2$ is hydrogen; or $R^2$ is phenyl.

In a specific aspect, $R^3$ is selected from —C(O)OR$^a$, —C(O)NR$^d$R$^e$, —OR$^f$, —NR$^b$R$^g$, —CN, $C_{3-6}$cycloalkyl, phenyl, and naphthyl, wherein $C_{3-6}$cycloalkyl is optionally substituted with one or two halo or with —OR$^a$, and phenyl is optionally substituted with one or two halo or with —CN;

In a specific aspect, $R^3$ is selected from —OR$^f$, $C_{3-6}$cycloalkyl, and phenyl, wherein $C_{3-6}$cycloalkyl is optionally substituted with one or two halo or with —OR$^a$, and phenyl is optionally substituted with one or two halo.

In another specific aspect, $R^3$ is selected from cyclopentyl, cyclohexyl, and phenyl, wherein cyclohexyl and phenyl are each optionally substituted with one or two fluoro. Representative $R^3$ groups within this aspect include, but are not limited to cyclopentyl, cyclohexyl, phenyl, 4,4-difluorocyclohexyl, 2,5-difluorophenyl, and the like.

In a specific aspect, $R^a$, $R^b$, $R^c$, and $R^d$ are each independently hydrogen or $C_{1-3}$alkyl.

In another specific aspect, $R^a$, $R^b$, $R^c$, and $R^d$ are each independently hydrogen or methyl.

In another specific aspect, $R^a$, $R^b$, $R^c$, and $R^d$ are each hydrogen.

In a specific aspect, $R^e$ is hydrogen or $C_{1-3}$alkyl, optionally substituted with $C_{3-6}$cycloalkyl, —$OR^a$, phenyl, pyridyl, or 4-phenylpiperazinyl; or $R^d$ and $R^e$ taken together with the nitrogen atom to which they are attached form piperidinyl.

In another specific aspect, $R^e$ is hydrogen or $C_{1-3}$alkyl, optionally substituted with phenyl or pyridyl.

In a specific aspect, $R^f$ is hydrogen, $C_{1-3}$alkyl, or phenyl.

In another specific aspect, $R^f$ is hydrogen.

In a specific aspect, $R^g$ is hydrogen or $C_{1-3}$alkyl, optionally substituted with phenyl.

In another specific aspect, $R^g$ is hydrogen or $C_{1-3}$alkyl.

In a specific aspect, m is 0, 1, or 2.

In separate aspects, m is 0; or m is 1; or m is 2.

In a specific aspect, the invention provides a compound of formula (I) wherein:

$R^1$ is selected from $C_{1-6}$alkyl, $C_{3-6}$cycloalkyl, and phenyl, wherein $C_{1-6}$alkyl is optionally substituted with one or two $R^3$, $C_{3-6}$cycloalkyl is optionally substituted with one or two halo or with —$OR^a$ or —$NR^bR^c$, and phenyl is optionally substituted with one or two halo or with —$OR^a$, —$NR^bR^c$, or $C_{1-4}$alkyl, wherein $C_{1-4}$alkyl is optionally substituted with —$OR^a$;

A is selected from triazolenyl, imidazolenyl, and oxadiazolenyl;

$R^2$ is hydrogen or phenyl;

$R^3$ is selected from —$OR^f$, $C_{3-6}$cycloalkyl, and phenyl, wherein $C_{3-6}$cycloalkyl is optionally substituted with one or two halo or with —$OR^a$, and phenyl is optionally substituted with one or two halo;

$R^a$, $R^b$, and $R^c$ are each independently hydrogen or $C_{1-3}$alkyl;

$R^f$ is hydrogen; and m is 0, 1, or 2;

or a pharmaceutically-acceptable salt thereof.

In another specific aspect, the invention provides a compound of formula (I) wherein:

$R^1$-A- is a moiety of formula (b);

$R^1$ is selected from —$C(O)OR^a$, —$C(O)NR^bR^c$, and $C_{1-3}$alkyl substituted with one $R^3$;

$R^2$ is phenyl;

$R^3$ is selected from —$OR^f$ and —$NR^bR^g$;

$R^a$, $R^b$, $R^c$, and $R^g$ are each independently hydrogen or $C_{1-3}$alkyl;

$R^f$ is hydrogen; and m is 2;

or a pharmaceutically-acceptable salt thereof.

In yet another aspect, the invention provides a compound of formula (Ia):

(Ia)

or a compound of formula (Ib):

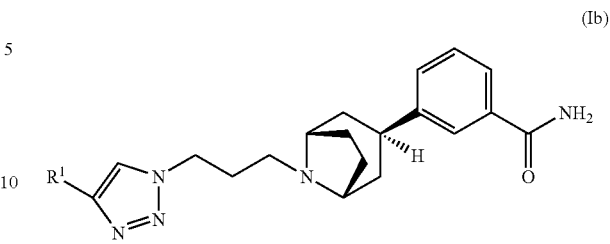

(Ib)

wherein $R^1$ takes any of the values defined above.

The invention further provides the compounds of Examples 1-72 herein.

The chemical naming convention used herein is illustrated for the compound of Example 1:

which is 3-endo-[8-(1-cyclohexyl-1H-[1,2,3]triazol-4-ylmethyl)-8-azabicyclo[3.2.1]oct-3-yl]benzamide. Alternatively, using the IUPAC conventions as implemented in AutoNom software, (MDL Information Systems, GmbH, Frankfurt, Germany), the compound is denoted 3-[(1R,3R,5S)-8-(1-cyclohexyl-1H-[1,2,3]triazol-4-ylmethyl)-8-azabicyclo[3.2.1]oct-3-yl]benzamide. The names used herein therefore correspond to the IUPAC notation with the endo orientation of the substituted phenyl group with respect to the 8-azabicyclo[3.2.1]octane group indicated explicitly. All of the compounds of the invention are in the endo orientation. For convenience, as used herein, the term "8-azabicyclooctane" means 8-azabicyclo[3.2.1]octane.

In addition to the endo stereochemistry with respect to the bicyclo group, the compounds of the invention may contain a chiral center in the substituent $R^1$ and at the carbon atom in formula (I) bearing the substituent $R^2$. Accordingly, the invention includes racemic mixtures, pure stereoisomers, and stereoisomer-enriched mixtures of such isomers, unless otherwise indicated. When the stereochemistry of a compound is specified, including both the orientation with respect to the 8-azabicyclooctane group and the chirality in a substituent $R^1$ or in the carbon atom bearing the substituent $R^2$, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "alkenyl" means a monovalent unsaturated hydrocarbon group containing at least one carbon-carbon double bond, typically 1 or 2 carbon-carbon double bonds, and which may be linear or branched or combinations thereof. Unless otherwise defined, such alkenyl groups typically contain from 1 to 10 carbon atoms. Representative alkenyl groups include, by way of example, vinyl, allyl, isopropenyl, but-2-enyl, n-pent-2-enyl, n-hex-2-enyl, n-hept-2-enyl, n-oct-2-enyl, n-non-2-enyl, n-dec-4-enyl, and the like.

The term "cycloalkyl" means a monovalent saturated or partially saturated carbocyclic group which may be monocyclic or multicyclic. Unless otherwise defined, such cycloalkyl groups typically contain from 3 to 12 carbon atoms. Representative cycloalkyl groups include, by way of example, cyclopropyl (c-propyl), cyclobutyl (c-butyl), cyclopentyl (c-pentyl), cyclohexyl (c-hexyl), cycloheptyl (c-heptyl), cyclooctyl (c-octyl), adamantyl, cyclohexenyl, and the like.

The term "heteroarylene" means a divalent aromatic cyclic group that contains at least one heteroatom, including one, two, three, or four heteroatoms, selected from N, O and S. For convenience, individual divalent heteroarylene rings may also be identified herein by the name of the corresponding isolated ring. For example, as used herein, the term "tetrazole" encompasses the isolated ring, a monovalent tetrazolyl and a divalent tetrazolenyl, where the valency of the ring is dictated by the structure of the species of which it is a part.

The term "halo" means fluoro, chloro, bromo or iodo.

The term "compound" means a compound that was synthetically prepared or prepared in any other way, such as by in vivo metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one general method of synthesis, compounds of formula (I) are prepared as illustrated in Scheme A. (The substituents and variables shown in the following schemes have the definitions provided above unless otherwise indicated).

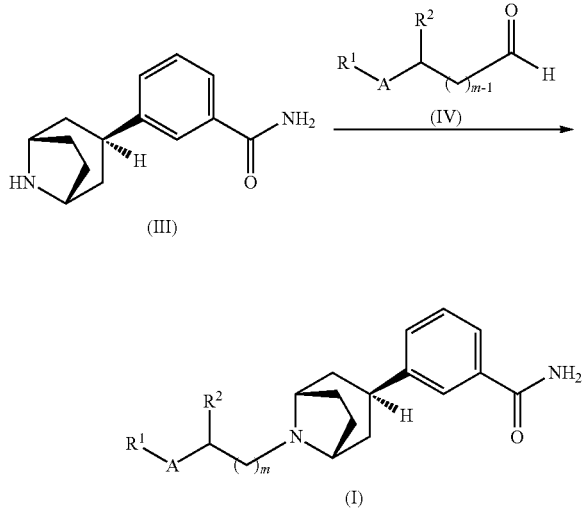

In this reaction, an intermediate of formula (III), is reductively N-alkylated by reaction with an aldehyde of formula (IV) to provide the product (I). The reaction is typically conducted by contacting intermediate (III) with between about 1 and about 2 equivalents of aldehyde (IV) in a suitable inert diluent, such as dichloromethane, in the presence of between about 0.9 and about 2 equivalents of a reducing agent. The reaction is typically conducted at a temperature in the range of about 0° C. to ambient temperature for about a half hour to about 3 hours or until the reaction is substantially complete. Typical reducing agents include sodium triacetoxyborohydride, sodium borohydride, and sodium cyanoborohydride. The product (I) is isolated by conventional means.

Alternatively, compounds of formula (I), where A is bonded to $R^1$ via a nitrogen atom on A, can be prepared by a two step process, in which an aldehyde of the formula (V) is coupled to intermediate (III) as described above to provide an intermediate (VI):

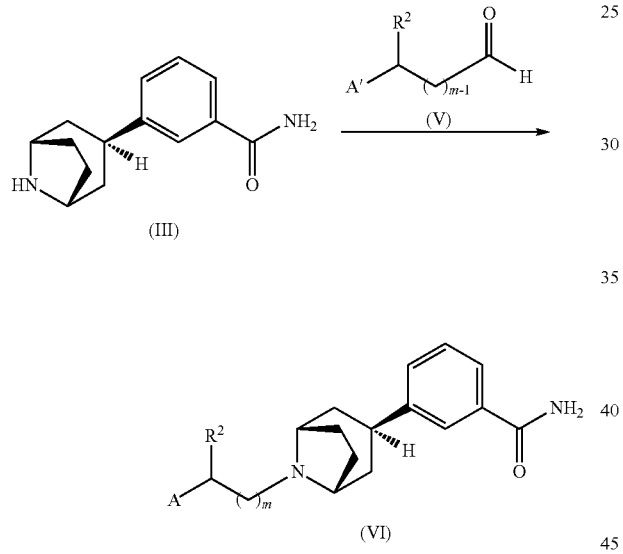

Scheme B

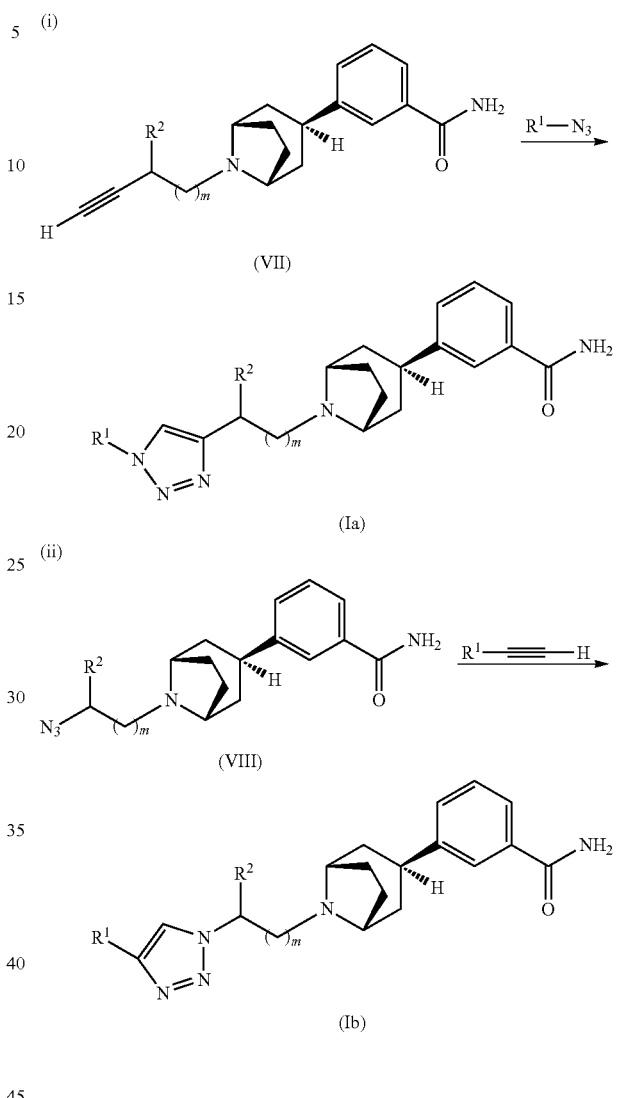

Scheme C where A' represents A or a protected form of A. When a protected form of A is used, the intermediate so formed is subsequently deprotected conventionally to provide intermediate (VI). For example, when A represents an imidazole ring, an intermediate (V) in which A' represents an N-benzyl imidazolyl may be used in the reaction of Scheme B. Intermediate (VI) is then reacted with a reagent of formula $R^1$—X, where X is a leaving group, preferably a sulfonate leaving group, to provide the product (I). For example, when X is methane sulfonate (commonly mesylate), intermediate (VI) is typically contacted with between about 1 and about 3 equivalents of $R^1$—X in the presence of between about 1 and about 3 equivalents of base. The reaction is typically conducted at a temperature in the range of about 80 to about 100° C. for between about 24 and about 80 hours or until the reaction is substantially complete.

Additional processes for preparing compounds of formula (Ia) or (Ib) where A is a triazole ring bonded as shown are illustrated in Scheme C:

in which the heteroarylene ring is formed by the reaction of an azide with an alkyne. The copper (I) catalyzed so-called "click" reaction has been found to be an efficient process for the formation of the heteroarylene ring, although the reaction of an azide with an alkyne can be promoted by heating, without use of a catalyst, as known to those skilled in the art. The click reaction to prepare a compound of formula (Ia) is typically conducted by contacting intermediate (VII) with between about 1 and about 1.2 equivalents of the azide $R^1$—$N_3$ in an inert diluent, typically a mixture of water and an alcohol partially miscible with water, in the presence of a catalytic amount of a mixture of copper(II), for example, copper(II)sulfate and a reducing agent, for example, sodium ascorbate, which produces copper(I) in situ. The reaction is typically conducted at ambient temperature for between about 10 and about 24 hours or until the reaction is substantially complete. Similarly, to prepare compounds of formula (Ib) in which m is 1 or 2, azide intermediate (VIII) is reacted with alkyne intermediate $R^1C\equiv CH$ to prepare a compound of formula (Ib) as shown in route (ii).

Compounds of formula (I) in which A is a tetrazole may be prepared by reactions similar to those of Scheme C above in which, in route (ii), R¹C≡CH is replaced by the corresponding nitrile R¹C≡N, and in route (i), the terminal alkyne of intermediate (VII) is replaced by an analogous intermediate with a terminal nitrile.

A process for the preparation of compounds of formula (Ic) where A is an oxadiazole is illustrated in Scheme D:

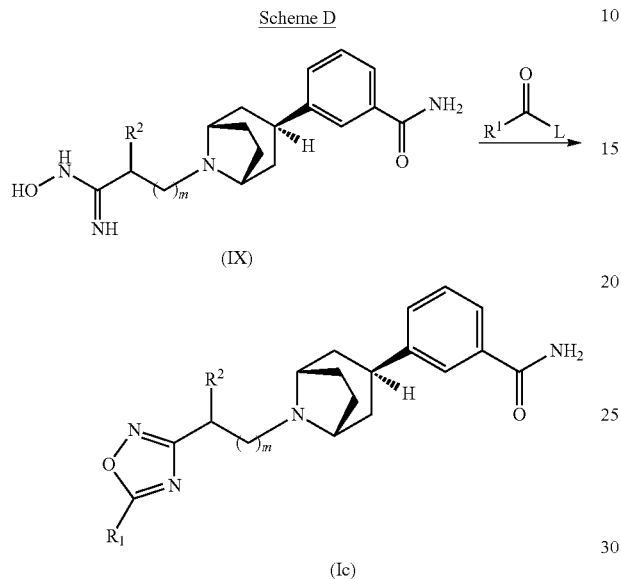

where L represents a halo leaving group, typically chloro. In the reaction of Scheme D, to form the oxadiazole ring, a carbamimido intermediate (IX) is contacted with between about 1 and about 1.2 equivalents of, for example, an acid chloride R¹C(O)Cl in an inert diluent in the presence of between about 3 and about 5 equivalents of base, for example N,N-diisopropylethyl amine. The reaction is typically conducted at a temperature in the range of about 80 to about 100° C. for between about 2 and about 10 hours or until the reaction is substantially complete.

As described in the examples below, in certain instances it is convenient to prepare compounds of formula (I) using a precursor, including a protected form, of the variable R¹ in place of R¹ in the above schemes, followed by a final step in which the precursor is transformed or deprotected in one or more steps to R¹.

The intermediates utilized in Schemes A through D above can be prepared from readily available starting materials. In particular, the 8-azabicyclooctane benzamide intermediate (III) can be prepared as illustrated in Scheme E:

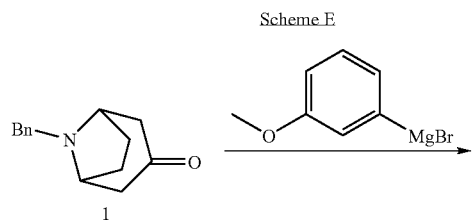

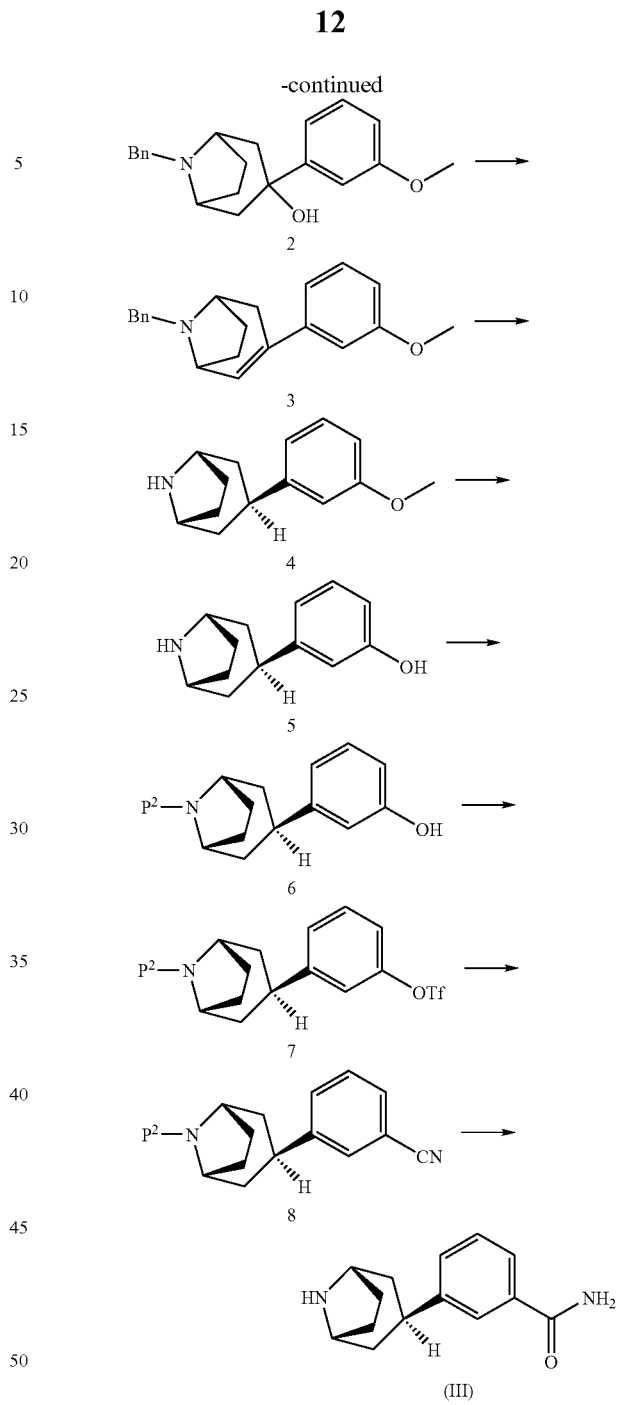

where Bn denotes the amino-protecting group benzyl, —OTf represents trifluoromethane sulfonate (commonly triflate) and P² represents an amino-protecting group, such as Boc or trifluoroacetyl. Protected 8-azabicyclo[3.2.1]octanone 1 is typically obtained from commercial sources and it can be prepared by the reaction of 2,5-dimethoxy-tetrahydrofuran with benzylamine and 1,3-acetonedicarboxylic acid in an acidic aqueous solution in the presence of a buffering agent as described in US 2005/0228014. (See also, U.S. Pat. No. 5,753,673).

First, intermediate 1 is added to a solution of between about 1 and about 2 equivalents of the Grignard reagent 3-methoxyphenyl magnesium bromide in an inert diluent. The reaction is typically conducted at a temperature of between about 0° C.

and about 10° C. for between about 1 and about 3 hours or until the reaction is substantially complete. Transmetalation of the Grignard reagent from magnesium to cerium by reaction with an equivalent amount of cerous chloride prior to use is advantageous for obtaining a good yield of intermediate 2. The hydroxy substituent is eliminated from intermediate 2 by treatment with aqueous 6N HCl to provide the hydrochloride salt of intermediate 3. This reaction is typically conducted at a temperature of between about 50° C. and about 100° C. for between about 1 and about 3 hours or until the reaction is substantially complete.

Hydrogenation of intermediate 3 saturates the double bond of the alkene moiety and removes the benzyl protecting group to provide intermediate 4. Crystallization of intermediate 4 as the hydrochloride salt provides 4 with high stereospecificity for the endo configuration. As described in Preparation 1(c) below, the exo impurity was undetected by high performance liquid chromatography (HPLC) analysis in the HCl salt of 4. Typically, the reaction is conducted by exposing the HCl salt of 3 dissolved in ethanol to a hydrogen atmosphere in the presence of a transition metal catalyst. The methyl group is removed from intermediate 4 by contacting a cooled solution of intermediate 4 in an inert diluent with between about 1 and about 2 equivalents of boron tribromide, hydrogen bromide, or boron trichloride. The reaction is typically conducted at a temperature of between about −80° C. and about 0° C. for between about 12 and about 36 hours or until the reaction is substantially complete. Intermediate 5 can be isolated by conventional procedures as a free base or as a hydrobromide salt. Crystallization of the hydrobromide salt provides intermediate 5 with high stereospecificity in the endo configuration.

When Boc is used as the protecting group, the phenol intermediate 5 is typically reacted with about 1 equivalent of di-tert-butyl dicarbonate (commonly Boc$_2$O) to provide the Boc-protected intermediate 6. The reactants are typically cooled to about 0° C. and then allowed to warm to ambient temperature over a period of between about 12 and about 24 hours. When trifluoroacetyl is used as the protecting group, typically 5 is reacted with about 2 equivalents of trifluoroacetyl anhydride to form the protected intermediate 6. Next, intermediate 6 in an inert diluent is contacted with a slight excess, for example about 1.1 equivalents of trifluoromethane sulfonyl chloride in the presence of between about 1 and about 2 equivalents of base to provide intermediate 7 which can be isolated by conventional procedures. Reaction of 7 with zinc cyanide in the presence of a transition metal catalyst, provides intermediate 8. This reaction is typically conducted at a temperature between about 60° C. and 120° C. under an inert atmosphere for about 2 to about 12 hours or until the reaction is substantially complete.

Finally, the nitrile intermediate 8 is hydrolyzed and deprotected to provide the carboxamide intermediate (III). Typically, in this reaction, when P$^2$ is Boc, intermediate 8 in an acidic solvent, for example trifluoroacetic acid, is contacted with between about 4 and about 6 equivalents of concentrated sulfuric acid. Typically the reaction is conducted in the temperature range of between about 50° C. and about 80° C. for about 8 to about 24 hours or until the reaction is substantially complete. The product is typically isolated in freebase form. When a trifluoroacetyl protecting group is used, the nitrile intermediate is first hydrolyzed to the carboxamide in concentrated sulfuric acid as described above. Quenching of the hydrolysis reaction by addition of base also removes the protecting group. The product is isolated as the freebase or as the hydrochloric acid salt.

The terminal alkyne intermediate (VII) of Scheme C is typically prepared by the conventional reaction of a reagent of the form HC≡CCH(R$^2$)(CH$_2$)$_m$X, where X is a halo or sulfonate leaving group, with the 8-azabicyclooctane benzamide intermediate (III). For example, when X is halo, the reaction is typically conducted by contacting intermediate (III) with between about 1 and about 2 equivalents of alkyl halide HC≡CCH(R$^2$)(CH$_2$)$_m$L in an inert diluent, such as ethanol, dimethylsulfoxide, or the like. The reaction is typically conducted at a temperature in the range of about 25° C. to about 80° C. for about a half hour to about 24 hours or until the reaction is substantially complete.

The azide reagents R$^1$—N$_3$ are conveniently prepared by the reaction of an intermediate R$^1$—X, where X is a leaving group such as a halo or a sulfonate leaving group, in particular toluene sulfonate (tosylate), with sodium azide. In general, the reaction is conducted by contacting a reagent R$^1$—X with between about 1 and about 2 equivalents of sodium azide in an inert diluent. The reaction is typically conducted at a temperature in the range of about 25° C. to about 90° C. for about one and a half hours to about 24 hours or until the reaction is substantially complete. Examples of the preparation of diverse azide reagents are provided below, including use of alternatives to sodium azide in the preparation of the reagents R$^1$—N$_3$.

The azide terminated intermediate (VIII) of Scheme C (ii) can be conveniently prepared by analogous reactions with sodium azide under similar reaction conditions. For example, an intermediate of formula (VIIIa) where m is 1 can be prepared by reaction of sodium azide with an intermediate of formula (X):

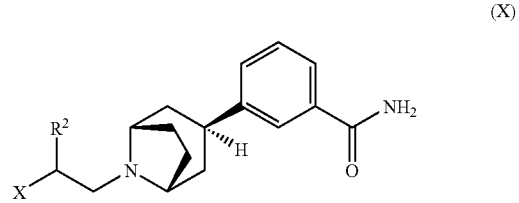

(X)

where X is a leaving group. For another example, an intermediate of formula (VIIIb) where m is 2 and R$^2$ is hydrogen may be obtained by reaction of sodium azide with an azetidine intermediate of formula (XI):

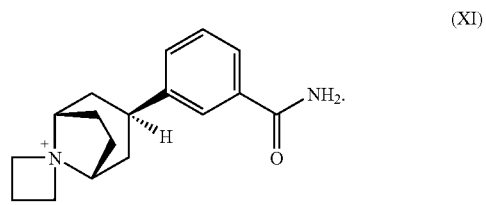

(XI)

Intermediates (X) and (XI) are typically prepared from the corresponding alcohols by reaction, for example, with methanesulfonyl chloride in the presence of an excess of base, such as N,N-diisopropylethylamine, as described in the examples below. The alcohol precursors to (X) and (XI) may be obtained by conventional alkyl halide coupling to the 8-azabicyclooctane benzamide intermediate (III).

Finally, intermediate (IX) of Scheme D may be prepared by reaction of intermediate (III) with a nitrile of the form N≡CCH(R²)(CH₂)$_m$L, where L is a halo leaving group, followed by reaction with hydroxylamine.

Further details regarding specific reaction conditions and other procedures for preparing representative compounds of the invention or intermediates thereto are described in the examples below.

Accordingly, in a method aspect, the invention provides a process for preparing a compound of formula (I), or a salt or protected derivative thereof, the process comprising (a) reacting a compound of formula (III) with a compound of formula (IV), or (b) (i) reacting a compound of formula (III) with a compound of formula (V) to provide a compound of formula (VI), and (ii) reacting a compound of formula (VI) with $R^1$—X to provide a compound of formula (I), or a salt or protected derivative thereof.

In addition, the invention provides a process for preparing a compound of formula (Ia), or a salt or protected derivative thereof, the process comprising reacting a compound of formula (VII) with $R^1$—$N_3$ to provide a compound of formula (Ia), or a salt or protected derivative thereof; and a process for preparing a compound of formula (Ib), or a salt or protected derivative thereof, the process comprising reacting a compound of formula (VIII) wherein m is 1 or 2 with $R^1C≡CH$ to provide a compound of formula (Ib), or a salt or protected derivative thereof.

In an additional aspect, the invention provides a compound of formula (VI), (VII), (VIII), and (IX), wherein the variables A, $R^2$ and m take any of the values described in aspects of the invention disclosed above.

Pharmaceutical Compositions

The 8-azabicyclooctane compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired. When discussing compositions, the "compound of the invention" may also be referred to herein as the "active agent". As used herein, the term "compound of the invention" is intended to include compounds of formula (I) as well as the species embodied in formulas (Ia), (Ib), and (Ic). "Compound of the invention" includes, in addition, pharmaceutically-acceptable salts and solvates of the compound unless otherwise indicated.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the compounds of the present invention may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, and 4-(4-{[(2-isopropyl- 1H-benzoimidazole-4-carbonyl)amino]methyl}-piperidin-1-ylmethyl)piperidine-1-carboxylic acid methyl ester and pharmaceutically-acceptable salts thereof may be used as the second therapeutic agent.

Additional useful prokinetic agents and other agents for gastrointestinal disorders include, but are not limited to, $5\text{-}HT_3$ receptor agonists (e.g. pumosetrag), $5\text{-}HT_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic $M_1$ and $M_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the compounds of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 μg/day to about 100 mg/day.

Accordingly, the pharmaceutical compositions of the invention optionally include a second therapeutic agent as described above.

The following examples illustrate representative pharmaceutical compositions of the present invention:

FORMULATION EXAMPLE A

Hard Gelatin Capsules for Oral Administration

A compound of the invention (50 g), spray-dried lactose (200 g) and magnesium stearate (10 g) are thoroughly blended. The resulting composition is loaded into a hard gelatin capsule (260 mg of composition per capsule).

FORMULATION EXAMPLE B

Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

FORMULATION EXAMPLE C

Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

FORMULATION EXAMPLE D

Tablets for Oral Administration

A compound of the invention (5 mg), starch (50 mg), and microscrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

FORMULATION EXAMPLE E

Tablets for Oral Administration

A compound of the invention (25 mg), microcrystalline cellulose (400 mg), fumed silicon dioxide (10 mg), and stearic acid (5 mg) are thoroughly blended and then compressed to form tablets (440 mg of composition per tablet).

FORMULATION EXAMPLE F

Single-scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

FORMULATION EXAMPLE G

Suspension for Oral Administration

The following ingredients are thoroughly mixed to form a suspension for oral administration containing 100 mg of active ingredient per 10 mL of suspension:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

FORMULATION EXAMPLE H

Dry Powder Composition

A micronized compound of the invention (1 mg) is blended with lactose (25 mg) and then loaded into a gelatin inhalation cartridge. The contents of the cartridge are administered using a powder inhaler.

FORMULATION EXAMPLE J

Injectable Formulation

A compound of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of the compounds of the invention, (i.e. free base, pharmaceutical salt, or solvate) that is suitable for the particular mode of administration, can be used in the pharmaceutical compositions discussed above.

Utility

The 8-azabicyclooctane compounds of the invention are antagonists at the mu opioid receptor and therefore are expected to be useful for treating medical conditions mediated by mu opioid receptors or associated with mu opioid receptor activity, i.e. medical conditions which are ameliorated by treatment with a mu opioid receptor antagonist. In particular, the compounds of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The mu opioid receptor antagonists of the invention are also expected to be useful for treating post-operative ileus, a disorder of reduced motility of the gastrointestinal tract that occurs after abdominal or other surgery. In addition, it has been suggested that mu opioid receptor antagonist compounds may be used for reversing opioid-induced nausea and vomiting. Further, those mu opioid receptor antagonists exhibiting some central penetration may be useful in the treatment of dependency on, or addiction to, narcotic drugs, alcohol, or gambling, or in preventing, treating, and/or ameliorating obesity.

Since compounds of the invention increase motility of the gastrointestinal (GI) tract in animal models, the compounds are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by mu opioid receptors, the compounds of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

As described above, compounds of the invention are mu opioid receptor antagonists. The invention further provides, therefore, a method of antagonizing a mu opioid receptor in a mammal, the method comprising administering a compound of the invention to the mammal.

The mu opioid receptor antagonists of the invention are optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

In addition, the compounds of the invention are also useful as research tools for investigating or studying biological systems or samples having mu opioid receptors, or for discovering new compounds having mu opioid receptor activity. Any suitable biological system or sample having mu opioid receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of contacting a biological system or sample comprising a mu opioid receptor with a compound of the invention are determined using conventional procedures and equipment, such as the radioligand binding assay and functional assay described herein or other functional assays known in the art. Such functional assays include, but are not limited to, ligand-mediated changes in intracellular cyclic adenosine monophosphate (cAMP), ligand-mediated changes in activity of the enzyme adenylyl cyclase, ligand-mediated changes in incorporation of analogs of guanosine triphosphate (GTP), such as [$^{35}$S] GTPγS (guanosine 5'-O-(γ-thio)triphosphate) or GTP-Eu, into isolated membranes via receptor catalyzed exchange of GTP analogs for GDP analogs, and ligand-mediated changes in free intracellular calcium ions. A suitable concentration of a compound of the invention for such studies typically ranges from about 1 nanomolar to about 500 nanomolar.

When using compounds of the invention as research tools for discovering new compounds have mu opioid receptor activity, binding or functional data for a test compound or a group of test compounds is compared to the mu opioid receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to exhibit potent binding to mu opioid receptors and little or no agonism in mu receptor functional assays. Therefore, the compounds of the invention are potent mu opioid receptor antagonists. Further, compounds of the invention have demonstrated predominantly peripheral activity as compared with central nervous system activity in animal models. Therefore, these compounds can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

AcOH=acetic acid
Boc=tert-butoxycarbonyl
$(Boc)_2O$=di-tert-butyl dicarbonate
DABCO=1,4-diazaobicylco[2,2,2]octane triethylenediamine
DCM=dichloromethane
DIPEA=N,N-diisopropylethylamine
DMA=dimethylacetamide
DMAP=dimethylaminopyridine
DMF=N,N-dimethylformamide
DMSO=dimethyl sulfoxide
EtOAc=ethyl acetate
EtOH=ethanol
HATU=N,N,N',N'-tetramethyl-O-(7-azabenzotriazol-1-yl)uronium hexafluorophosphate
MeCN=acetonitrile
MeOH=methanol
MeTHF=2-methyltetrahydrofuran
MTBE=tert-butyl methyl ether
PyBop=benzotriazol-1-yloxytripyrrolidino-phosphonium hexafluorophosphate
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

Preparation 1:
3-endo-(8-Azabicyclo[3.2.1]oct-3-yl)benzamide a. 8-Benzyl-3-exo-(3-methoxyphenyl)-8-azabicyclo[3.2.1]octan-3-ol To a 3 L flask was added cerous chloride powder (194 g, 0.79 mol). The flask was flushed with nitrogen and THF (800 mL) was added. The reaction mixture was stirred at 25° C. for 1 h. To the mixture was added ~1M 3-methoxyphenyl magnesium bromide in THF (800 mL, 0.87 mol) dropwise. The resulting slurry was stirred at 3° C. for 1.5 hours. A solution of 8-benzyl-8-aza-bicyclo[3.2.1]octan-3-one (120.4 g, 0.56 mol) in THF (200 mL) was then added dropwise, while maintaining the internal temperature at −5° C. The resulting solution was stirred for 15 min. The reaction mixture was added to a flask containing 6 N HCl (800 mL) maintaining the temperature at 10° C. After solvent was removed by rotary evaporation, the reaction mixture was stirred at room temperature overnight. The solids were isolated by filtration, washed with 6N HCL (70 mL) and acetonitrile (3×70 mL), and dried to provide the HCl salt of the title intermediate as an off-white solid (161 g).

b. 8-Benzyl-3-(3-methoxyphenyl)-8-azabicyclo[3.2.1]oct-2-ene

To a 3 L flask was added 8-benzyl-3-exo-(3-methoxyphenyl)-8-azabicyclo[3.2.1]octan-3-ol hydrochloride (383.9 g, 1.06 mol), 6 M HCl (800 mL), and MeTHF (200 mL). The resulting slurry was heated at 70° C. for 2.5 h under nitrogen. The reaction mixture was transferred to a 12 L reactor and cooled to 10° C. The reaction flask was washed with MeTHF (1 L) that was added to the 12 L reactor. NaOH (50 wt % in water, 200 mL) was added and additional NaOH (50 wt %, 150 mL) was added in portions until pH ~13 was reached. The phases were separated, the water layer was extracted with MeTHF (1 L), and combined MeTHF layers were washed with brine (1 L). Solvent was reduced by rotary evaporation at 30 to 40° C. yielding the title intermediate (360 g) as a thick oil. EtOH (1.5 L) was added and the volume was reduced to ~500 mL and then adjusted to 1.8 L.

c. 3-endo-(3-Methoxyphenyl)-8-azabicyclo[3.2.1]octane

To 8-benzyl-3-(3-methoxyphenyl)-8-azabicyclo[3.2.1]oct-2-ene (in EtOH 95%, 400 mL, 0.20 mol), prepared in the previous step, was added 6 M HCl (45 mL) and then MeTHF (50 mL). The reaction mixture was purged with nitrogen, heated to 40° C. and palladium on carbon (10 weight %, 8 g) was added. The reactor was pressurized with hydrogen (3×20 psi) and then hydrogenated at 20 psi at 40° C. for 18 h. The reaction mixture was filtered through Celite, concentrated, washed with MeTHF (2×100 mL), filtered through a coarse glass filter, washed with MeTHF (10 mL) and dried on the filter to provide the HCl salt of the title intermediate as white solid (31 g, single isomer, (exo isomer undetectable by HPLC)). An additional 5.2 g of product was recovered from the mother liquor.

d. 3-endo-(8-Azabicyclo[3.2.1]oct-3-yl)-phenol

To a 500 mL flask was added 3-endo-(3-methoxyphenyl)-8-azabicyclo[3.2.1]octane hydrochloride (115 g, 0.45 mol) and hydrobromic acid (48 weight % in water, 100 mL, 0.88 mol). The mixture was heated to 120° C. and held at that temperature for 24 h with stirring. Additional hydrobromic acid solution (25 mL) was added and the reaction mixture was heated with stirring for 6 h and then cooled to 70° C. Acetonitrile (200 mL) was added and the resulting slurry was cooled to 10° C. and then filtered, and the filter cake was washed with acetonitrile (50 mL) to yield the HBr salt of the title intermediate (99 g, >99% pure) as a white granular solid.

e. 2,2,2-Trifluoro-1-[3-endo-(3-hydroxyphenyl)-8-azabicyclo[3.2.1]oct-8-yl]ethanone To a solution of 3-endo-(8-azabicyclo[3.2.1]oct-3-yl)-phenol hydrobromide (54.4 g, 0.19 mol), toluene (210 mL), and triethylamine (40 mL, 0.29 mol), was added trifluoroacetic anhydride (54 mL, 0.38 mol) over 20 min. The reaction mixture was stirred at 40° C. for 2 h. Ethyl acetate (370 mL) and brine in water (1:1, 265 mL) were added. The reaction mixture was stirred for 15 min, the phases were separated. To the organic layer was added saturated sodium bicarbonate (300 mL) and the mixture was stirred vigorously overnight. The phases were separated and the organic layer was washed with brine in water (1:1, 265 mL) dried over sodium sulfate and most of the solvent was removed by rotary evaporation. Toluene (100 mL) was added and the solvent removed by rotary evaporation to provide the crude title intermediate.

f. Trifluoromethanesulfonic acid 3-endo-[8-(2,2,2-trifluoroacetyl)-8-azabicyclo[3.2.1]oct-3-yl]phenyl ester To a 500 mL flask was added the ethyl acetate solution (220 mL) of the intermediate of the previous step (32.8 g, 0.11 mol) and triethylamine (23 mL. 0.17 mol). The solution was cooled to 5° C. and trifluoromethane sulfonyl chloride (14 mL, 0.13 mol) was added dropwise. The mixture was allowed to warm to 25° C. and stirred at that temperature for 1 h. Saturated sodium bicarbonate (200 mL) was added, the layers were separated, brine (150 mL) was added to the organic layer, the layers were again separated, and solvent was removed from the organic layer to provide the crude title intermediate.

g. 3-endo-[8-(2,2,2-Trifluoroacetyl)-8-azabicyclo[3.2.1]oct-3-yl]-benzonitrile

To a 100 mL flask was added trifluoromethanesulfonic acid 3-endo-[8-(2,2,2-trifluoro-acetyl)-8-azabicyclo[3.2.1]oct-3-yl]phenyl ester (25.3 g, 58.7 mmol), tris(dibenzylideneacetone)dipalladium (0) (0.81 g, 0.9 mmol), 1,1'-bis(diphenylphosphino)ferrocene
(1.01 g, 1.8 mmol), and zinc cyanide (4.2 g, 35.8 mmol). Three times, the flask was purged with nitrogen for 5 min and then placed under house vacuum for 5 min. To the flask was added DMF (150 mL) and distilled water (2.5 mL). The solution was purged with nitrogen with stirring for 10 min, heated to 120° C. and stirred at 120° C. under nitrogen for 4 h. When the reaction was completed 20 g of product from a previous lot, prepared by the same procedure, was added and stirred for 20 min.

Most of the solvent was removed by distillation and the solution was cooled to 22° C. To the solution was added ethyl acetate (445 mL) and the resulting solution was filtered through Celite. Sodium bicarbonate (450 mL) was added and the solution was stirred for 15 min. The layers were separated and the organic layer was washed with diluted brine (2×95 mL), and filtered through sodium sulfate. The volume was reduced to about 50 mL by removal of ethyl acetate. Isopropyl alcohol (150 mL) was added and the solution was agitated at 22° C. for 1 h. Solids were isolated by filtration and washed with isopropyl alcohol (2×25 mL) to provide the title intermediate (33.5 g, 100% pure by HPLC) as an off-white/light brown solid. A second crop of product (6.3 g, >98% pure by HPLC) was isolated from the filtrate.

h. 3-endo-(8-Azabicyclo[3.2.1]oct-3-yl)benzamide

A solution of 3-endo-[8-(2,2,2-trifluoroacetyl)-8-azabicyclo[3.2.1]oct-3-yl]-benzonitrile (10 g, 32 mmol) in sulfuric acid (96%, 12 mL) was heated to 50° C. with stirring and held at that temperature with stirring for 2 h. The reaction mixture was cooled to 22° C. and added slowly to a 500 mL flask containing 5 N NaOH (90 mL) and methanol (100 mL) which was cooled to 10° C. Salt precipitates were filtered and the filtrate was stirred at 22° C. for 1 h. The reaction mixture was concentrated under reduced pressure. To the residue was added MeTHF (150 mL) and the reaction mixture was stirred at 22° C. for 5 min. The layers were separated and MeTHF (100 mL) was added to the aqueous layer. The layers were separated and brine (150 mL) was added to the combined organic layers. The layers were separated and the organic layer was dried over potassium carbonate and filtered, and the solvent was removed. A mixture of EtOH (25 mL) and concentrated HCl (2.6 mL) was added to the residue with stirring and then MTBE (25 mL) was added and the solution was stirred at 22° C. Precipitated solids were filtered and air dried to provide the HCl salt of the title compound (8 g, 97% purity by HPLC) as a white solid.

Preparation 2: 3-endo-(8-Prop-2-ynyl-8-azabicyclo [3.2.1]oct-3-yl)benzamide

Propargyl bromide (80 mol % wt in toluene) (0.742 mL, 6.66 mmol) was added to a stirred solution of 3-endo-(8-azabicyclo[3.2.1]oct-3-yl)-benzamide (1.53 g, 6.66 mmol) and DIPEA (2.32 mL, 13.31 mmol) in ethanol (25 mL) at room temperature, under an atmosphere of nitrogen. After 24 h, the reaction mixture was concentrated in vacuo and the residue partitioned between chloroform (100 mL) and 1M NaOH (25 mL). The organic layer was separated, washed with brine (25 mL), dried (MgSO4), filtered and concentrated in vacuo. The residue was purified by flash chromatography (chloroform and then 90% chloroform:[methanol: ammonium hydroxide 9:1]) to afford the title compound (1.36 g). $^1$H NMR (400 MHz; CDCl$_3$): δ (ppm): 7.80 (d, 1H), 7.59 (m, 1H), 7.43 (m, 1H), 7.32 (m, 1H), 6.45 (bs, 2H), 3.44 (m, 2H), 3.11-3.18 (m, 3H), 2.40-2.47 (m, 2H), 2.23 (m, 1H), 1.92-1.96 (m, 2H), 1.62-1.68 (m, 2H), 1.45-1.50 (m, 2H); (m/z); [M+H]$^+$ calcd for C$_{27}$H$_{32}$N$_6$O$_2$ 269.17; found: 269.2.

Preparation 3: 3-endo-[8-(2-Azidoethyl)-8-azabicyclo[3.2.1]oct-3-yl]-benzamide a. 3-endo-[8-(2-Hydroxyethyl)-8-azabicyclo[3.2.1]oct-3-yl]-benzamide Bromoethanol (0.222 mL, 3.13 mmol) was added to a stirred solution of 3-endo-(8-azabicyclo[3.2.1]oct-3-yl)-benzamide (600 mg, 2.61 mmol) and DIPEA (1.36 mL, 7.83 mmol) in ethanol (10 mL) at room temperature, under an atmosphere of nitrogen. The reaction mixture was heated to 60° C. and after 30 min and after 4 h an additional amount of bromoethanol (0.111 mL, 1.56 mmol) was added. After an additional 12 h, the reaction mixture was concentrated in vacuo to afford the title compound which was used without further purification. (m/z): [M+H]+ calcd for $C_{16}H_{22}N_2O_2$ 275.18; found 275.0.

b. 3-endo-[8-(2-Chloroethyl)-8-azabicyclo[3.2.1]oct-3-yl]-benzamide

Methanesulfonyl chloride (0.264 mL, 3.39 mmol) was added to a stirred suspension of the crude product of the previous step (2.61 mmol) in DIPEA (4.09 mL, 23.48 mmol) and dichloromethane (20 mL) at room temperature, under an atmosphere of nitrogen. After 1 h and 2.5 h an additional amount of methanesulfonyl chloride (0.264 mL, 3.39 mmol) was added. After an additional 12 h, the reaction mixture was concentrated in vacuo and the residue diluted with chloroform (40 mL) and washed with aqueous NaHCO₃ (15 mL) and brine (15 mL). The organic layer was dried (MgSO4), filtered and concentrated in vacuo to afford the title compound as a crude oil which was used without further purification. (m/z): [M+H]+ calcd for $C_{16}H_{21}ClN_2O$ 293.14; found 293.2.

c. 3-endo-[8-(2-Azidoethyl)-8-azabicyclo[3.2.1]oct-3-yl]benzamide

Sodium azide (238 mg, 3.65 mmol) was added to a stirred solution of the crude product of the previous step (2.61 mmol) in DMF (20 mL) at room temperature, under an atmosphere of nitrogen. After 18 h, the reaction mixture was concentrated to about 5 mL, diluted with ethyl acetate (70 mL) and washed with water (20 mL). The aqueous layer was further extracted with ethyl acetate (2×70 mL), basified with aqueous NaHCO₃ (10 mL) and again extracted with ethyl acetate (50 mL) and chloroform (50 mL). The organic layers were combined, dried (MgSO4), filtered and concentrated in vacuo. The residue was purified by flash chromatography (chloroform and then 95% chloroform:[methanol: ammonium hydroxide 9:1]) to afford the title compound (507 mg). ¹H NMR (400 MHz; CDCl₃) δ (ppm): 7.63 (s, 1H), 7.45 (d, 1H), 7.30 (d, 1H), 7.19 (dd, 1H), 6.14 (bs, 2H), 3.11-3.20 (m, 4H), 2.97-3.02 (m, 1H), 2.38-2.41 (m, 2H), 2.25-2.35 (m, 2H) 1.80-1.84 (m, 2H), 1.32-1.43 (m, 4H); (m/z): [M+H]+ calcd for $C_{16}H_{21}N_5O$ 300.18; found 300.2.

Preparation 4: 3-endo-[8-(2-Azidopropyl)-8-azabicyclo[3.2.1]oct-3-yl]-benzamide a. 3-endo-[8-(2-Hydroxypropyl)-8-azabicyclo[3.2.1]oct-3-yl]benzamide Bromopropanol (0.173 mL, 1.91 mmol) was added to a stirred solution of 3-endo-(8-azabicyclo[3.2.1]oct-3-yl)-benzamide (400 mg, 1.74 mmol) and DIPEA (0.91 mL, 5.22 mmol) in ethanol (7 mL) at room temperature, under an atmosphere of nitrogen. The reaction mixture was heated to 60° C. and after 4 h a further amount of bromopropanol (0.024 mL, 0.26 mmol) was added. After an additional 12 h, the reaction mixture was concentrated in vacuo to afford the title compound which was used without further purification.

b. 3-endo-(3-Carbamoylphenyl)spiro[azetidine-1,8'-bicyclo[3.2.1]octan]-1-ium methanesulfonate Methanesulfonyl chloride (0.253 mL, 3.26 mmol) was added to a stirred suspension of the crude product of the previous step (1.74 mmol) in DIPEA (2.73 mL, 15.66 mmol) and DCM (20 mL) at room temperature under an atmosphere of nitrogen. After 3 h an additional amount of methanesulfonyl chloride (0.135 mL, 1.74 mmol) was added. After an additional 60 h, the reaction mixture was concentrated in vacuo to afford the title compound as a crude oil which was used without further purification. (m/z): [M]+ calcd for $C_{17}H_{23}N_2O$ 271.18; found 271.0.

c. 3-endo-[8-(2-Azidopropyl)-8-azabicyclo[3.2.1]oct-3-yl]benzamide

Sodium azide (136 mg, 2.09 mmol) was added to a stirred solution of the crude product of the previous step (1.74 mmol) in DMF (15 mL) at room temperature, under an atmosphere of nitrogen. After 60 h, the reaction mixture was quenched by the addition of water (10 mL), basified with aqueous NaHCO₃ (10 mL) and extracted with ethyl acetate (3×50 mL) and chloroform (2×20 mL). The organic layers were combined, dried (MgSO4), filtered and concentrated in vacuo. The residue was purified by flash chromatography (chloroform and then 95% chloroform:[methanol: ammonium hydroxide 9:1]) to afford the title compound (315 mg). (m/z): [M+H]+ calcd for $C_{17}H_{23}N_5O$ 314.20; found 314.3.

Preparation 5: 3-endo-{8-[3-(N-Hydroxycarbamimidoyl)-propyl]-8-azabicyclo[3.2.1]oct-3-yl}benzamide To a solution of 3-endo-(8-azabicyclo[3.2.1]oct-3-yl)-benzamide (111.3 mg, 0.48 mmol) in EtOH (1.5 mL) at room temperature was added DIPEA (124.1 mg, 0.96 mmol) followed by 4-bromobutanenitrile (71.0 mg, 0.48 mmol). The resulting mixture was heated at 70° C. for 1 h and then cooled to ambient temperature for 60 h and then heated to 70° C. for 8 h before it was cooled to ambient temperature overnight. The reaction mixture was then treated with 50% aqueous hydroxylamine (95.0 mg, 1.44 mmol) at room temperature overnight. Additional 50% aqueous hydroxylamine (95.0 mg, 1.44 mmol) was added and the reaction mixture was stirred overnight, concentrated, and the residue was dissolved in water (4.0 mL). The solution was acidified to pH~3.0 with conc. HCl. The mixture was filtered and purified by reverse phase preparative HPLC to give the title compound as its bis TFA salt (118.9 mg). (m/z): [M+H]+ calcd for $C_{18}H_{26}N_4O_2$ 331.20; found 331.4.

Preparation 6: Cyclohexylmethyl azide

Cyclohexylmethyl bromide (200 mg, 1.13 mmol) was added to a stirred solution of 0.5 M sodium azide in DMSO (2.48 mL, 1.24 mmol) at room temperature, under an atmosphere of nitrogen. After 21 h, the reaction was quenched by the addition of water (5 mL) and extracted with diethyl ether (3×4 mL). The combined organic layers were washed with brine (5 mL), dried (MgSO₄), filtered and concentrated in vacuo to afford the title compound as a crude oil (136 mg) which was used without further purification.

Preparation 7: Cyclohexyl azide

Cyclohexyl bromide (2.74 mL, 0.023 mol) was added to a stirred solution of 0.5M sodium azide in DMSO (50 mL, 0.025 mol) at room temperature, under an atmosphere of nitrogen. The reaction mixture was heated to 75° C. behind a blast shield and stirred for 5 h. The reaction mixture was then cooled with an ice-bath, quenched by the addition of water (75 mL) and extracted with diethyl ether (3×125 mL). The combined organic layers were washed with brine (75 mL),

Preparation 8: 2-Azidocyclohexanol

To a solution of 7-oxa-bicyclo[4.1.0]heptane (0.300 g, 3.06 mmol) in acetone (3 mL) was added sodium azide (0.504 g, 7.75 mmol) in water (3 mL). The reaction mixture was refluxed for 12 h. The acetone was removed in vacuo and the product was extracted with ethyl acetate (5 mL). The organic layer was collected, dried over anhydrous sodium sulfate, filtered, and concentrated to provide the title compound (46 mg).

Preparation 9: 4-Azidomethyl-1,1-difluorocyclohexane a. (4,4-Difluorocyclohexyl)methanol To a solution of 4,4-difluorocyclohexanecarboxylic acid ethyl ester (0.50 g, 2.6 mmol) cooled to 0° C. in diethyl ether (20 mL) was added dropwise 1.0 M lithium aluminum hydride in tetrahydrofuran (2.6 mL, 2.6 mmol). The reaction was stirred for 30 min. The reaction was carefully quenched with water (2.0 mL) followed by the addition of 1.0 N NaOH (2 mL). The reaction mixture was stirred for 10 min, filtered through a pad of celite and washed with diethyl ether (20 mL). The organic layer was collected, dried over anhydrous magnesium sulfate, filtered, and concentrated to give the title compound as a crude oil (465 mg) which was used without further purification.

b. Toluene-4-sulfonic acid 4,4-difluorocyclohexylmethyl ester

To a solution of the crude product of the previous step (465 mg, 0.31 mmol) and triethylenediamine (0.346 mg, 0.31 mmol) cooled to 0° C. in dichloromethane (20 mL) was added a p-toluenesulfonylchloride (0.589 g, 0.31 mmol) in dichloromethane (5 mL). The reaction mixture was stirred overnight and then washed with 0.5 N HCl (20 mL). The organic layer was collected, dried over anhydrous sodium sulfate, filtered, and concentrated. The crude product was purified by flash column chromatography to give the title compound as a white solid (748 mg).

c. 4-Azidomethyl-1,1-difluorocyclohexane

To a solution of toluene-4-sulfonic acid 4,4-difluorocyclohexylmethyl ester (100 mg, 0.33 mmol)) in N,N-Dimethylformamide (0.5 mL) was added sodium azide (32 mg, 0.49 mmol). The reaction mixture was stirred at 90° C. for 90 min, cooled to room temperature and diluted with dichloromethane (5 mL). The organic layer was washed with water (2×5 mL), collected, dried over anhydrous sodium sulfate, filtered, and concentrated to provide the title compound which was used without further purification.

Preparation 10: 3-Azidomethylpentane a. Toluene-4-sulfonic acid 2-ethylbutyl ester To a solution of 2-ethyl-1-butanol (1.00 g, 9.79 mmol), triethylenediamine (1.32 g, 11.7 mmol) in DCM (30 mL, 0.5 mol) cooled to 0° C. was added p-toluenesulfonyl chloride (1.96 g, 10.3 mmol) in DCM (10 mL) The reaction mixture was stirred for 30 min, and extracted with 1.0N NaOH (2×40 mL). The organic layer was collected, dried over anhydrous sodium sulfate, filtered, and isolated by rotary evaporation to give the title compound (2.40 g).

b. 3-Azidomethylpentane

To a solution of the product of the previous step (2.40 g, 9.36 mmol) in DMF (15 mL, 0.19 mol) was added sodium azide (0.86 g, 13.2 mmol). The reaction mixture was heated at 80° C. overnight, cooled to room temperature, diluted with diethyl ether (50 mL) and washed with water (3×75mL). The organic layer was collected, dried over anhydrous sodium sulfate, filtered, and concentrated at room temperature under light vacuum to give the title compound (1.0 g).

Preparation 11: 1-Benzyl-1H-imidazole-4-carbaldehyde

To a solution of imidazolecarboxaldehyde (1.0 g, 10.4 mmol) in DMF (10 mL) was added sodium carbonate (2.2 g, 20.8 mmol). The mixture was then treated with a solution of benzyl bromide (1.77 g, 10.4 mmol) in DMF (5 mL) dropwise and stirred for 1 h at 100° C. The reaction mixture was partitioned between EtOAc and water, and the aqueous layer was extracted with EtOAc. The organic layers were combined, dried with MgSO$_4$, filtered, and concentrated to yield a dark brown oil (1.14 g). (m/z): [M+H]$^+$ calcd for C$_{11}$H$_{10}$N$_2$O 187.21; found, 187.3. $^1$H NMR (d6-DMSO, 400 MHz) δ (ppm): 9.67 (s, 1H), 8.22, 8.08, 7.96, 7.90 (4 sets of singlets, total 2H), 7.30-7.24 (m, 5H), 5.49 (s, 1H), 5.25 (s, 1H).

Preparation 12: 1-Cyclohexyl-1H-imidazole-4-carbaldehyde

To a solution of imidazolecarboxaldehyde (60 mg, 0.63 mmol) in DMF (0.4 mL) was added sodium carbonate (132 mg, 1.26 mmol). The mixture was then treated with a solution of cyclohexylbromide (152 mg, 0.94 mmol) in DMF (0.4 mL) dropwise and stirred at 90° C. for 72 h. The reaction mixture was partitioned between EtOAc (2 mL) and water (2 mL), and the aqueous layer was extracted with EtOAc. The organic layers were combined, dried with Na$_2$SO$_4$, filtered, and concentrated to yield to yield the title compound which was used without further purification (66 mg). (m/z): [M+H]$^+$ calcd for C$_{10}$H$_{14}$N$_2$O 179.11; found, 179.2.

Preparation 13: 3-endo-[8-(3H-Imidazol-4-ylmethyl)-8-aza-bicyclo[3.2.1]oct-3-yl]-benzamide a. 3-endo-[8-(3-Benzyl-3H-imidazol-4-ylmethyl)-8-aza-bicyclo[3.2.1]oct-3-yl]-benzamide To a suspension of the HCl salt of 3-endo-(8-azabicyclo[3.2.1]oct-3-yl)-benzamide (600 mg, 2.25 mmol) in DCM (15 mL) was added 3-benzyl-3H-imidazole-4-carbaldehyde (502 mg, 2.70 mmol) followed by sodium triacetoxyborohydride (572 mg, 2.70 mmol). The solution was stirred overnight. The reaction mixture was diluted with DCM and washed with saturated NaHCO$_3$ and brine. The organic layer was dried with MgSO$_4$, filtered, concentrated, and purified by reverse phase preparative HPLC to provide the mono-TFA salt of the title intermediate (432 mg). (m/z): [M+H]$^+$ calcd for C$_{25}$H$_{28}$N$_4$O 401.23; found 401.6.

b. 3-endo-[8-(3H-Imidazol-4-ylmethyl)-8-aza-bicyclo[3.2.1]oct-3-yl]-benzamide

To a solution of the product of the previous step in ethanol (10 mL) was added palladium hydroxide (20% by weight, 86 mg). The reaction vessel was purged three times under a balloon of hydrogen and the reaction mixture was stirred overnight. The palladium residue was filtered using a Millipore filter and rinsed with EtOH. The organic layer was concentrated to yield a white solid (320 mg). (m/z): [M+H]+ calcd for $C_{18}H_{22}N_4O$ 311.18; found 311.4.

Preparation 14: 3-endo-[8-((S)-3-Azido-3-phenylpropyl)-8-azabicyclo[3.2.1]oct-3-yl]benzamide a. Toluene-4-sulfonic acid (S)-3-hydroxy-3-phenylpropyl ester To a solution of (S)-1-phenyl-propane-1,3-diol (0.5 g, 3.3 mmol) and triethylenediamine (368 mg, 3.3 mmol) in DCM (40 mL) cooled to 0° C. was added dropwise p-toluenesulfonyl chloride (1.96 g, 0.0103 mol) in DCM (20 mL). The reaction mixture was stirred for 1 h and then filtered through a pad of silica. The silica was washed with DCM and the filtrate was concentrated to give the title compound as a crude oil (0.485 mg).

b. 3-endo-[8-((S)-3-Azido-3-phenylpropyl)-8-azabicyclo[3.2.1]oct-3-yl]benzamide

To a solution of the product of the previous step (485 mg, 1.57 mmol) and sodium bicarbonate (198 mg, 2.4 mmol) in dimethyl sulfoxide (10 mL) was added 3-endo-(8-aza-bicyclo[3.2.1]oct-3-yl)benzamide (362 mg, 1.6 mmol). The reaction mixture was stirred at 90° C. for 5 h, cooled to room temperature, diluted with ethyl acetate (50 mL) and washed with water (3×50 mL). The organic layer was collected, dried over anhydrous sodium sulfate, filtered, and concentrated.

To a solution of the resulting solid and 1,8-diazabicyclo[5.4.0]undec-7-ene (470 μL, 3.1 mmol) in DCM (50 mL) cooled to 0° C. was added diphenylphosphonic azide (680 μL, 3.1 mmol). The reaction mixture was stirred for 2 days at room temperature. The reaction mixture was washed with water (2×50 mL) and filtered through a pad of celite. The organic layer was collected, dried over anhydrous sodium sulfate, filtered, and concentrated. The crude product was purified by preparative HPLC and extracted with dichloromethane and 1.0 N NaOH to give the title compound (165 mg). (m/z): [M+H]+ calcd for $C_{23}H_{27}N_5O$, 390.22; found 390.3.

Example 1

3-endo-[8-(1-Cyclohexyl-1H-[1,2,3]triazol-4-ylmethyl)-8-azabicyclo[3.2.1]oct-3-yl]benzamide Cyclohexyl azide (466 mg, 3.73 mmol) was added to a stirred suspension of 3-endo-(8-prop-2-ynyl-8-azabicyclo[3.2.1]oct-3-yl)benzamide in tert-butanol/water (1:1, 25 mL). A solution of 1M sodium ascorbate in water (0.373 mL, 0.373 mmol) was added to the reaction mixture followed by copper sulfate pentahydrate (9 mg, 0.037 mmol) and the reaction vigorously stirred behind a blast shield for 15 h. The reaction mixture was concentrated in vacuo and the residue diluted with AcOH/water (1:1), filtered and purified by preparative HPLC to afford the title compound. $^1$H NMR (400 MHz; CDCl$_3$) δ (ppm): 8.20 (s, 1H), 8.05 (s, 1H), 7.76 (m, 1H), 7.48 (m, 1H), 4.55 (m, 1H), 4.31 (s, 2H), 4.13 (s, 2H), 2.74-2.78 (m, 2H), 2.50-2.56 (m, 2H), 2.18-2.27 (m, 4H), 1.76-1.97 (m, 8H), 1.48-1.60 (m, 2H), 1.35 (m, 1H); (m/z): [M+H]+ calcd for $C_{23}H_{31}N_5O$ [394.26; found 394.5.

Example 2

3-endo-{8-[1-((2R,3R)-2-Hydroxycyclohexyl)-1H-1,2,3-triazol-4-ylmethyl]-8-azabicyclo[3.2.1]oct-3-yl}benzamide To a solution of 3-endo-(8-prop-2-ynyl-8-azabicyclo[3.2.1]oct-3-yl)benzamide (80 mg, 0.30 mmol) and 2-azidocyclohexanol (46 mg, 0.33 mmol) in water (0.5 mL) and tert-butanol (0.5 mL) was added (+)-sodium L-ascorbate (32 mg, 0.016 mmol) and a few grains of copper(II)sulfate pentahydrate. The reaction mixture was stirred for 12 h, concentrated, and purified by preparative HPLC to give the title compound as the TFA salt (55.7 mg). (m/z): [M+H]+ calcd for $C_{23}H_{31}N_5O_2$, 410.25; found 410.2.

Examples 3 and 4

3-endo-{8-[1-(4-Fluorocyclohex-3-enyl)-1H-1,2,3-triazol-4-ylmethyl]-8-azabicyclo[3.2.1]oct-3-yl}benzamide (EX3) and 3-endo-{8-[1-(4,4-Difluorocyclohexyl)-1H-1,2,3-triazol-4-ylmethyl]-8-azabicyclo [3.2.1]oct-3-yl}benzamide (EX4)

a. Toluene-4-sulfonic acid 1,4-dioxa-spiro[4.5]dec-8-yl ester

To a solution of 1,4-dioxa-spiro[4.5]decan-8-ol (1.0 mg, 6.3 mmol) and triethylenediamine (0.780 mg, 7.0 mmol) cooled to 0° C. in DCM (20 mL) was added p-toluenesulfonylchloride (1.31 g, 7.0 mmol) in DCM (5 mL). The reaction mixture was stirred overnight and then washed with 0.5 N HCl (20 mL). The organic layer was collected, dried over anhydrous sodium sulfate, filtered, and concentrated to give the title compound (2.0 g) which was used without further purification.

b. 3-endo-{8-[1-(1,4-Dioxa-spiro[4.5]dec-8-yl)-1H-1,2,3-triazol-4-ylmethyl]-8-azabicyclo[3.2.1]oct-3-yl}benzamide To a solution of the crude product of the previous step in DMF (15 mL) was added sodium azide (0.617 mg, 9.5 mmol). The reaction mixture was stirred at 80° C. for 5 h, cooled to room temperature and diluted with ethyl acetate (50 mL). The organic layer was washed with water (2×50 mL). The organic layer was collected, dried over anhydrous sodium sulfate, filtered, and concentrated at room temperature. To the resulting crude oil and 3-endo-(8-prop-2-ynyl-8-azabicyclo[3.2.1]oct-3-yl)benzamide (1.8 g, 6.7 mmol) in water (10 mL) and tert-butanol (10 mL) was added (+)-sodium L-ascorbate (696 mg, 3.51 mmol) and copper(II)sulfate pentahydrate (100 mg, 0.40 mmol). The reaction mixture was stirred for 12 h, diluted with ethyl acetate (50 mL) and washed with water (50 mL). The organic layer was collected, dried over anhydrous sodium sulfate, filtered, and concentrated to give the title compound (2.2 g) which was used without further purification. (m/z): [M+H]+ calcd for $C_{25}H_{33}N_5O_3$, 452.26; found 452.2.

c. 3-endo-{8-[1-(4-Oxocyclohexyl)-1H-1,2,3-triazol-4-ylmethyl]-8-azabicyclo[3.2.1]oct-3-yl}benzamide A solution of the crude product of the previous step (2.2 g, 4.9 mmol) in a mixture of acetic acid (5 mL), water (10 mL), and trifluoroacetic acid (400 μL) was stirred at 90° C. for 4 h. The reaction mixture was cooled to room temperature and purified by preparative HPLC. The resulting TFA salt was suspended in DCM (50 mL) and washed with a mixture of brine (45 mL) and 6.0N NaOH (5 mL). The organic layer was collected, dried over anhydrous sodium sulfate, filtered, and concentrated to give the title compound (1.4 g). (m/z): [M+H]+ calcd for $C_{23}H_{29}N_5O_2$, 408.23; found 408.4.

d. 3-endo-{8-[1-(4-Fluorocyclohex-3-enyl)-1H-1,2,3-triazol-4-ylmethyl]-8-azabicyclo[3.2.1]oct-3-yl}benzamide (EX3) and 3-endo-{8-[1-(4,4-Difluorocyclohexyl)-1H-1,2,3-triazol-4-ylmethyl]-8-azabicyclo[3.2.1]oct-3-yl}benzamide (EX4)

To a solution of 3-endo-{8-[1-(4-oxocyclohexyl)-1H-1,2,3-triazol-4-ylmethyl]-8-aza-bicyclo[3.2.1]oct-3-yl}benzamide (280 mg, 0.687 mmol) in DCM (10 mL) was added diethylaminosulfur trifluoride (100 μL, 76 mmol). The reaction mixture was stirred for 15 h at room temperature, diluted with DCM (10 mL) and carefully quenched with water (5 mL). The reaction was basified to pH 14 with 6.0 N NaOH. The organic layer was collected, dried over anhydrous sodium sulfate, filtered, and concentrated. The crude product was purified by preparative HPLC to give the title compounds as the TFA salt: EX3 (90.6 mg) (m/z): [M+H]$^+$ calcd for $C_{23}H_{28}FN_5O$, 410.23; found 410.4 EX4 (35 mg) (m/z): [M+H]$^+$ calcd for $C_{23}H_{29}F_2N_5O$, 430.23; found 430.4.

Example 5

3-endo-{8-[1-(4-Fluorocyclohexyl)-1H-1,2,3-triazol-4-ylmethyl]-8-azabicyclo [3.2.1]oct-3-yl}benzamide To a solution of 3-endo-{8-[1-(4-fluorocyclohex-3-enyl)-1H-1,2,3-triazol-4-ylmethyl]-8-azabicyclo[3.2.1]oct-3-yl-benzamide TFA salt (80 mg, 0.152 mmol) in methanol (5 mL) was added palladium (10% wt on activated carbon, 16 mg). The reaction mixture was stirred overnight under an atmosphere of hydrogen. The catalyst was removed by filtration, the filtrate was concentrated, and purified by preparative HPLC to give the two stereoisomers at the cyclohexyl ring of the title compound as their TFA salts. (21.0 mg and 12.5 mg) (m/z): [M+H]$^+$ calcd for $C_{23}H_{30}FN_5O$, 412.24; found 412.4.

Example 6

3-endo-{8-[1-(4-Hydroxycyclohexyl)-1H-1,2,3-triazol-4-ylmethyl]-8-azabicyclo[3.2.1]oct-3-yl}benzamide To a solution of 3-endo-{8-[1-(4-oxocyclohexyl)-1H-1,2,3-triazol-4-ylmethyl]-8-azabicyclo[3.2.1]oct-3-yl}benzamide (100 mg, 0.25 mmol) in tetrahydrofuran (2 mL) and methanol (1 mL) was added sodium borohydride (10 mg, 0.26 mmol). The reaction mixture was stirred for 1 h at room temperature, concentrated and purified by preparative HPLC to give the two stereoisomers at the cyclohexyl ring of the title compound as their TFA salts. (91.4 mg and 20.7 mg) (m/z): [M+H]$^+$ calcd for $C_{23}H_{31}N_5O_2$, 410.25; found 410.2.

Example 7

3-endo-(8-{1-[(Benzylmethyl-carbamoyl)methyl]-1H-[1,2,3]triazol-4-ylmethyl}-8-azabicyclo[3.2.1]oct-3-yl)benzamide a. 4-[3-endo-(3-Carbamoyl-phenyl)-8-aza-bicyclo[3.2.1]oct-8-ylmethyl]-[1,2,3]triazol-1-yl}-acetic acid Lithium hydroxide (34 mg, 0.82 mmol) was added to a stirred solution of 4-[3-endo-(3-carbamoyl-phenyl)-8-azabicyclo[3.2.1]oct-8-ylmethyl]-[1,2,3]triazol-1-yl}-acetic acid ethyl ester (270 mg, 0.68 mmol) in ethanol (10 mL) at room temperature. After 30 min, the reaction mixture was concentrated in vacuo. The residue was diluted with 1M HCl (5 mL) and the solution concentrated in vacuo (×2) to afford the title compound which was used without further purification. (m/z): [M+H]$^+$ calcd for $C_{19}H_{23}N_5O_3$ 370.19; found 370.2.

b. 3-endo-(8-{1-[(Benzylmethyl-carbamoyl)methyl]-1H-[1,2,3]triazol-4-ylmethyl}-8-azabicyclo[3.2.1]oct-3-yl)benzamide N-Benzylmethylamine (0.019 mL, 0.15 mmol) and HATU (57 mg, 0.15 mmol) were added to a stirred solution of the product of the previous step (28 mg, 0.076 mmol) and DIPEA (0.039 mL, 0.23 mmol) in DMF (1 mL) at room temperature. After 2 h 30 min, the reaction mixture was concentrated in vacuo, diluted with AcOH/water (1:1, 1 mL), filtered and purified by preparative HPLC to afford the title compound. (m/z): [M+H]$^+$ calcd for $C_{27}H_{32}N_6O_2$ 473.27; found 473.4.

Example 8

3-endo-{8-[2-(4-Propyl-[1,2,3]triazol-1-yl)-ethyl]-8-aza-bicyclo[3.2.1]oct-3-yl}benzamide 1-Pentyne (0.01 mL, 0.10 mmol) was added to a stirred suspension of 3-endo-[8-(2-azidoethyl)-8-azabicyclo[3.2.1]oct-3-yl]-benzamide (30 mg, 0.10 mmol) in tert-butanol/water (1:1, 1.5 mL). A solution of 1 M sodium ascorbate in water (0.01 mL, 0.01 mmol) was added to the reaction mixture followed by copper sulfate pentahydrate (1 mg) and the reaction mixture was stirred vigorously. After 14 h, additional 1-pentyne (0.02 mL, 0.20 mmol) was added and the reaction mixture stirred for 4 h. The reaction mixture was concentrated in vacuo and the residue diluted with AcOH/water (1:1), filtered and purified by preparative HPLC to afford the title compound (5.1 mg) (m/z): [M+H]$^+$ calcd for $C_{21}H_{29}N_5O$ 368.25; found 368.2.

Example 9

3-endo-(8-{3-[4-(2,4-Difluorophenyl)-[1,2,3]triazol-1-yl]-propyl}-8-azabicyclo[3.2.1]oct-3-yl)benzamide A solution of 3-endo-[8-(2-azidopropyl)-8-azabicyclo[3.2.1]oct-3-yl]benzamide (37 mg, 0.12 mmol) in tert-butanol/water (1:1, 1 mL) was added to 1-ethynyl-2,4-difluorobenzene (17 mg, 0.12 mmol). A solution of 1M sodium ascorbate in water (0.012 mL, 0.012 mmol) was added to the reaction mixture followed by copper sulfate pentahydrate (1 mg) and the reaction stirred vigorously. After 14 h, the reaction mixture was concentrated in vacuo and the residue diluted with AcOH/water (1:1), filtered and purified by preparative HPLC to afford the title compound (9.4 mg). (m/z): [M+H]$^+$ calcd for $C_{25}H_{27}F_2N_5O$ 452.52; found 452.2.

Example 10

3-endo-[8-(1-Benzyl-1H-imidazol-4-ylmethyl)-8-aza-bicyclo[3.2.1]oct-3-yl]benzamide To a suspension of the mono-HCl salt form of 3-endo-(8-aza-bicyclo[3.2.1]oct-3-yl)benzamide hydrochloride (50 mg, 0.22 mmol) in dichloromethane (1 mL) was added 1-benzyl-1H-imidazole-4-carbaldehyde (61 mg, 0.33 mmol) followed by sodium triacetoxyborohydride (70 mg, 0.33 mmol). The reaction mixture was stirred overnight, diluted with DCM and washed with saturated NaHCO$_3$ and brine. The organic layer was dried with Na$_2$SO$_4$, filtered, concentrated, and purified by reverse phase preparative HPLC to provide the mono-TFA salt of the title compound (43.2 mg). (m/z): [M+H]$^+$ calcd for $C_{25}H_{28}N_4O$ 401.23; found 401.2.

Example 11

3-endo-[8-(3-Benzyl-1H-imidazol-4-ylmethyl)-8-aza-bicyclo[3.2.1]oct-3-yl]-benzamide Following a procedure similar to that of Example 10, using the reagent 3-benzyl-1H-imidazole-4-carbaldehyde, the title compound was prepared. (m/z): [M+H]$^+$ calcd for $C_{25}H_{28}N_4O$ 401.23; found 401.2.

Examples 12 and 13

3-endo-{8-[3-(4,4-Difluorocyclohexylmethyl)-3H-imidazol-4-ylmethyl]-8-azabicyclo[3.2.1]oct-3-yl}benzamide (EX 12) and 3-endo-{8-[1-(4,4-Difluorocyclohexylmethyl)-1H-imidazol-4-ylmethyl]-8-azabicyclo[3.2.1]oct-3-yl}benzamide (EX13)

a. (4,4-Difluorocyclohexyl) methanol

To a solution of 4,4-difluorocyclohexanecarboxylic acid ethyl ester (150 mg, 0.78 mmol) in diethylether (5 mL) at 0° C. was added a 2 M solution of lithium aluminum hydride in THF (0.39 mL, 0.78 mmol) dropwise. The reaction mixture was stirred at 0° C. for one h. The reaction was quenched with water (1 mL) and 1N NaOH (2 mL) was added, forming a white slurry. The aqueous layer with extracted with EtOAc (2×10 mL) and the organic layers combined, washed with brine, dried with $Na_2SO_4$, filtered, and concentrated to yield a clear oil. $^1$H NMR (CD$_3$OD, 400 MHz) δ (ppm): 3.38 (d, J=6.4 Hz, 2H), 2.05-1.97 (m, 2H), 1.83-1.64 (m, 4H), 1.58-1.50 (m, 1H), 1.29-1.19 (m, 2H).

b. Methanesulfonic acid 4,4-difluorocyclohexylmethyl ester

To a solution of the product of the previous step (117 mg, 0.78 mmoL) in DCM (4 mL) at 0° C. was added DIPEA (101 mg, 0.78 mmol). To the reaction mixture was added a solution of methanesulfonyl chloride (89 mg, 0.78 mmol) in DCM (0.5 mL). After 2 h the reaction was diluted with DCM, washed with saturated $NaHCO_3$, 1N HCl, and brine. The organic layer was dried with $Na_2SO_4$, filtered, and concentrated to yield a white solid (95 mg). $^1$H NMR (CD$_3$OD, 400 MHz) δ (ppm): 4.08 (d, J=6.0 Hz, 2H), 3.04 (s, 3H), 2.05-2.01 (m, 2H), 1.87-1.73 (m, 4H), 1.56-1.49 (m, 1H), 1.39-1.21 (m, 2H).

c. 3-endo-{8-[3-(4,4-Difluorocyclohexylmethyl)-3H-imidazol-4-ylmethyl]-8-azabicyclo[3.2.1]oct-3-yl}benzamide (EX 12) and 3-endo-{8-[1-(4,4-Difluorocyclohexylmethyl)-1H-imidazol-4-ylmethyl]-8-azabicyclo[3.2.1]oct-3-yl}benzamide (EX13)

To a vial was added 3-endo-[8-(3H-imidazol-4-ylmethyl)-8-aza-bicyclo[3.2.1]oct-3-yl]-benzamide (50.0 mg, 0.161 mmol) and sodium carbonate (34.1 mg, 0.322 mmol) in DMF (0.8 mL, 10 mmol). Methanesulfonic acid 4,4-difluorocyclohexylmethyl ester (73.5 mg, 0.322 mmol) was added and the reaction mixture was stirred at 100° C. for about 72 h and then concentrated. The two products were separated and purified by reverse phase preparative HPLC to provide the mono-TFA salts of the title compounds EX12 (7.6 mg) and EX13 (6.7 mg). (m/z): [M+H]$^+$ calcd for $C_{25}H_{32}F_2N_4O$ 443.25; found 443.2.

Example 14

3-endo-{8-[3-(5-Isobutyl-1,2,4-oxadiazol-3-yl)-propyl]-8-aza-bicyclo[3.2.1]oct-3-yl}benzamide To a solution of 3-endo-{8-[3-(N-hydroxycarbamimidoyl)propyl]-8-aza-bicyclo[3.2.1]oct-3-yl}benzamide bis TFA salt (40.0 mg, 0.07 mmol) in DMA (0.4 mL) at room temperature was added DIPEA (36.2 mg, 0.28 mmol) followed by isovaleryl chloride (10.08 mg, 0.084 mmol). The resulting mixture was heated at 92° C. for 4 h and then concentrated. The residue was dissolved in 50% AcOH/H$_2$O (1.5 mL), filtered, and purified by reverse phase preparative HPLC to give the title compound as its bis TFA salt. (3.1 mg) (m/z): [M+H]+ calcd for $C_{23}H_{32}N_4O_2$ 397.25; found 397.4.

Examples 15-72

Using processes similar to those of Examples 1-15, the compounds of Tables 1 to 6 were prepared.

TABLE 1

| Ex No | R$^1$ | Formula | Calc. [M + H]$^+$ | Obs. [M + H]$^+$ |
|---|---|---|---|---|
| 15 | adamantan-1-yl | $C_{27}H_{35}N_5O$ | 446.28 | 446.4 |
| 16 | benzyl | $C_{24}H_{27}N_5O$ | 402.22 | 402.5 |
| 17 | —CH$_2$C(O)OC$_2$H$_5$ | $C_{21}H_{27}N_5O_3$ | 398.21 | 398.3 |
| 18 | —CH$_2$C(O)NHCH$_2$-c-hexyl | $C_{26}H_{36}N_6O_2$ | 465.29 | 465.4 |
| 19 | —CH$_2$C(O)N(CH$_3$)—(CH$_2$)$_2$OH | $C_{22}H_{30}N_6O_3$ | 427.24 | 427.2 |
| 20 | —CH$_2$C(O)N(C$_2$H$_5$)-pyridinyl | $C_{27}H_{33}N_7O_2$ | 488.27 | 488.4 |
| 21 | —CH$_2$C(O)-piperidin-1-yl | $C_{24}H_{32}N_6O_2$ | 437.26 | 437.4 |
| 22 | —CH$_2$C(O)NH-benzyl | $C_{26}H_{30}N_6O_2$ | 459.24 | 459.4 |
| 23 | —CH$_2$C(O)-(4-phenyl-piperazin-1-yl) | $C_{29}H_{35}N_7O_2$ | 514.29 | 514.4 |
| 24 | —CH$_2$-c-hexyl | $C_{24}H_{33}N_5O$ | 408.27 | 408.2 |
| 25 | —CH$_2$-(4,4-difluoro-c-hexyl) | $C_{24}H_{31}F_2N_5O$ | 444.25 | 444.2 |
| 26 | —CH$_2$(C$_2$H$_5$)$_2$ | $C_{22}H_{31}N_5O$ | 382.25 | 382.4 |
| 27 | —CH$_2$CH(C$_2$H$_5$)$_2$ | $C_{23}H_{33}N_5O$ | 396.27 | 396.4 |

TABLE 2

| Ex. No. | R$^1$ | Formula | Calc. [M + H]$^+$ | Obs. [M + H]$^+$ |
|---|---|---|---|---|
| 28 | phenyl | $C_{24}H_{27}N_5O$ | 402.22 | 402.2 |
| 29 | —(CH$_2$)$_2$-phenyl | $C_{26}H_{31}N_5O$ | 430.25 | 430.2 |
| 30 | —CH$_2$N(CH$_3$)-benzyl | $C_{27}H_{34}N_6O$ | 459.28 | 459.4 |

TABLE 2-continued

[Structure: R¹-triazole-CH₂CH₂-N-bicyclic-phenyl-C(O)NH₂]

| Ex. No. | R¹ | Formula | Calc. [M + H]⁺ | Obs. [M + H]⁺ |
|---|---|---|---|---|
| 31 | 2,4-difluorophenyl | $C_{24}H_{25}F_2N_5O$ | 438.20 | 438.2 |
| 32 | 4-hydroxymethyl-phenyl | $C_{25}H_{29}N_5O_2$ | 432.23 | 432.2 |
| 33 | 4-t-butylphenyl | $C_{28}H_{35}N_5O$ | 458.28 | 458.4 |
| 34 | 3-hydroxyphenyl | $C_{24}H_{27}N_5O_2$ | 418.22 | 418.2 |
| 35 | c-pentyl | $C_{23}H_{31}N_5O$ | 394.25 | 394.4 |
| 36 | 4-aminophenyl | $C_{24}H_{28}N_6O$ | 417.23 | 417.2 |
| 37 | —CH₂-c-pentyl | $C_{24}H_{33}N_5O$ | 408.27 | 408.4 |
| 38 | t-butyl | $C_{22}H_{31}N_5O$ | 382.25 | 382.2 |
| 39 | —CH₂O-phenyl | $C_{25}H_{29}N_5O_2$ | 432.23 | 432.2 |
| 40 | benzyl | $C_{25}H_{29}N_5O$ | 416.24 | 416.2 |
| 41 | 1-amino-c-hexyl | $C_{24}H_{34}N_6O$ | 423.28 | 423.4 |
| 42 | —CH(OH)-phenyl | $C_{25}H_{29}N_5O_2$ | 432.23 | 432.2 |
| 43 | —CH₂-c-hexyl | $C_{25}H_{35}N_5O$ | 422.28 | 422.4 |

TABLE 3

[Structure with chiral center]

| Ex. No. | R¹ | Formula | Calc. [M + H]⁺ | Obs. [M + H]⁺ |
|---|---|---|---|---|
| 44 | —C(O)OH | $C_{26}H_{29}N_5O_3$ | 460.23 | |
| 45 | —CH₂OH | $C_{26}H_{31}N_5O_2$ | 446.25 | |
| 46 | —CH₂N(C₂H₅)₂ | $C_{30}H_{40}N_6O$ | 501.33 | 501.4 |
| 47 | —C(O)NH₂ | $C_{26}H_{30}N_6O_2$ | 459.24 | 459.4 |
| 48 | —CH₂OH | $C_{26}H_{31}N_5O_2$ | 446.25 | 446.2 |
| 49 | —C(O)OH | $C_{26}H_{29}N_5O_3$ | 460.23 | 460.2 |

* Denotes chiral center. Examples 44 and 49 and 45 and 48 have opposite stereochemistry at this center.

TABLE 4

[Structure: R¹-triazole-(CH₂)₃-N-bicyclic-phenyl-C(O)NH₂]

| Ex. No. | R¹ | Formula | Calc. [M + H]⁺ | Obs. [M + H]⁺ |
|---|---|---|---|---|
| 50 | 4-t-butylphenyl | $C_{29}H_{37}N_5O$ | 472.30 | 472.4 |
| 51 | 4-aminophenyl | $C_{25}H_{30}N_6O$ | 431.25 | 431.2 |
| 52 | —CH₂O-phenyl | $C_{26}H_{31}N_5O_2$ | 446.25 | 446.2 |
| 53 | benzyl | $C_{26}H_{31}N_5O$ | 430.25 | 430.2 |
| 54 | 1-amino-c-hexyl | $C_{25}H_{36}N_6O$ | 437.30 | 437.4 |
| 55 | —CH₂-c-hexyl | $C_{26}H_{37}N_5O$ | 436.30 | 436.4 |

TABLE 5

[Structure: R¹-imidazole-CH₂-N-bicyclic-phenyl-C(O)NH₂]

| Ex. No. | R¹ | Formula | Calc. [M + H]⁺ | Obs. [M + H]⁺ |
|---|---|---|---|---|
| 56 | c-hexyl | $C_{24}H_{32}N_4O$ | 393.26 | 393.2 |
| 57 | —CH₂-c-hexyl | $C_{25}H_{34}N_4O$ | 407.27 | 407.2 |
| 58 | —(CH₂)₂-c-hexyl | $C_{26}H_{36}N_4O$ | 421.29 | 421.4 |
| 59 | —CH₂-naphthyl | $C_{29}H_{30}N_4O$ | 451.24 | 451.2 |
| 60 | —CH₂-(4-cyano-phenyl) | $C_{26}H_{27}N_5O$ | 426.22 | 426.2 |
| 61 | —CH₂-(2,6-difluorophenyl) | $C_{25}H_{26}F_2N_4O$ | 437.21 | 437.2 |
| 62 | —CH₂-c-propyl | $C_{22}H_{28}N_4O$ | 365.23 | 365.2 |
| 63 | —CH₂CH(C₂H₅)₂ | $C_{24}H_{34}N_4O$ | 395.27 | 395.2 |
| 64 | —(CH₂)₂CH₃ | $C_{21}H_{28}N_4O$ | 353.23 | 353.2 |
| 65 | —(CH₂)₄CH₃ | $C_{23}H_{32}N_4O$ | 381.26 | 381.2 |
| 66 | —(CH₂)₂CN | $C_{21}H_{25}N_5O$ | 364.21 | 364.2 |
| 67 | —CH₂CH=CH₂ | $C_{21}H_{26}N_4O$ | 351.21 | 351.2 |

TABLE 6

[Structure: R¹-oxadiazole-(CH₂)₃-N-bicyclic-phenyl-C(O)NH₂]

| Ex. No. | R¹ | Formula | Calc. [M + H]⁺ | Obs. [M + H]⁺ |
|---|---|---|---|---|
| 68 | —CH₂OC(O)CH₃ | $C_{22}H_{28}N_4O_4$ | 413.21 | 413.2 |
| 69 | benzyl | $C_{26}H_{30}N_4O_2$ | 431.24 | 431.2 |
| 70 | —CH(C₂H₅)₂ | $C_{24}H_{34}N_4O_2$ | 411.27 | 411.4 |
| 71 | c-pentyl | $C_{24}H_{32}N_4O_2$ | 409.25 | 409.4 |
| 72 | c-hexyl | $C_{25}H_{34}N_4O_2$ | 423.27 | 423.4 |

Assay 1: Radioligand Binding Assay on Human Mu, Human Delta and Guinea Pig Kappa Opioid Receptors a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin-100 μg/mL streptomycin and 800 μg/mL Geneticin in a 5% $CO_2$, humidified incubator @37° C. Receptor expression levels ($B_{max}$ ~2.0 and ~0.414 pmol/mg protein, respectively) were determined using [³H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 μL containing the appropriate amount of membrane protein (~3, ~2 and ~20 μg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 μM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM naloxone. $K_i$ values for test compounds were calculated, in Prism, from the best fit $IC_{50}$ values, and the $K_d$ value of the radioligand, using the Cheng-Prusoff equation ($K_i=IC_{50}/(1+([L]/K_d))$ where [L]=the concentration of [$^3$H]-Diprenorphine. Results are expressed as the negative decadic logarithm of the $K_i$ values, $pK_i$.

Test compounds having a higher $pK_i$ value in these assays have a higher binding affinity for the mu, delta, or kappa opioid receptor. The compounds of Examples 1-72 were tested in these assays. All of the compounds had a $pK_i$ value between about 7.0 and about 10.6 at the human mu opioid receptor. For example, the compounds of Examples 1, 4, 8, 9, 11, and 14 had $pK_i$ values of 10.3, 10.0, 10.1, 10.3, 9.2, and 8.8, respectively. Compounds of the invention also exhibited $pK_i$ values between about 5.7 and about 10.1 at the human delta and guinea pig kappa opioid receptors.

Assay 2: Agonist mediated activation of the mu-opioid receptor in membranes prepared from CHO-K1 cells expressing the human mu-opioid receptor In this assay, the potency and intrinsic activity values of test compounds were determined by measuring the amount of bound GTP-Eu present following receptor activation in membranes prepared from CHO-K1 cells expressing the human mu opioid receptor.

a. Mu Opioid Receptor Membrane Preparation:

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 pmol/mg protein, respectively. Protein concentration was determined using a Bio-Rad Bradford Protein Assay kit. Membranes were stored in frozen aliquots at −80° C., until required. Lyophilized GTP-Eu and GDP were diluted to 10 μM and 2 mM, respectively, in double distilled $H_2O$ then mixed and permitted to sit at room temperature for 30 minutes prior to transfer to individual aliquots samples for storage at −20° C.

b. Human mu GTP-Eu Nucleotide Exchange Assay

GTP-Eu nucleotide exchange assays were performed using the DELPHIA GTP-binding kit (Perkin/Elmer) in AcroWell 96 well filter plates according to the manufacturer's specifications. Membranes were prepared as described above, and prior to the start of the assay, aliquots were diluted to a concentration of 200 μg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 μM into Assay Buffer containing 0.1% BSA, and serial (1:5) dilutions then made to generate ten concentrations of compound ranging from 40 pM⁻ 80 μM-GDP and GTP-Eu were diluted to 4 μM and 40 nM, respectively, in Assay Buffer. The assay was performed in a total volume of 100 μL containing 5 μg of membrane protein, test compound ranging from 10 pM-20 μM), 1 μM GDP, and 10 nM GTP-Eu diluted in 10 mM $MgCl_2$, 50 mM NaCl, and 0.0125% BSA, (final assay concentrations). A DAMGO (Tyr-D-Ala-Gly-(methyl)Phe-Gly-ol) concentration-response curve (ranging from 12.8 pM-1 μM) was included on every plate.

Assay plates were prepared immediately prior to assay following the addition of 25 μL of Assay Buffer, 25 μL of test compound, and 25 μL GDP and GTP-Eu. The assay was initiated by the addition of 25 μL membrane protein and allowed to incubate for 30 minutes. The assay plates were then filtered with a Waters vacuum manifold connected to the house vacuum regulated to 10-12 in. Hg and washed with room temperature GTP Wash Solution (2×300 mL). The bottoms of the plates were blotted to remove excess liquid. The plates were then immediately read to determine the amount of bound GTP-Eu by measuring Time Resolved Fluorescence (TRF) on a Packard Fusion Plate ReaderVehicle: DMSO not to exceed 1% final assay concentration.

The amount of bound GTP-Eu is proportional to the degree of activation of the mu opioid receptors by the test compound. The intrinsic activity (IA), expressed as a percentage, was determined as the ratio of the amount of bound GTP-Eu observed for activation by the test compound to the amount observed for activation by DAMGO which is presumed to be a full agonist (IA=100). With the exception of Examples 44 and 49, the compounds of Examples 1 to 72 demonstrated intrinsic activities in this assay of less than about 20, typically less than about 10. For example, the compounds of Examples 1, 4, 8, 9, 11, and 14 had IA values of −4, 0, −4, −1, 6, and −11, respectively. Thus, the compounds of the present invention have been shown to act as antagonists at the human mu opioid receptor.

Assay 3: Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (©1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit $ID_{50}$ values were calculated. Curve minima and maxima were fixed to loperamide control values (indicating 0% reversal) and vehicle controls (indicating 100% reversal), respectively. Results are expressed as $ID_{50}$, the dose required for 50% reversal of the effects of loperamide, in milligrams per kilogram. The compounds of Examples 1 and 4, administered orally, exhibited $ID_{50}$ values of 0.13 mg/kg and 0.25 mg/kg, respectively in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

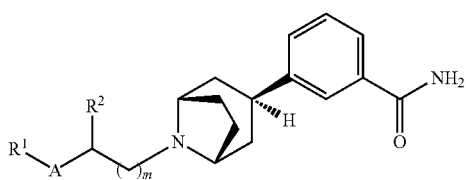

(I)

wherein:

A is a five-membered heteroarylene ring containing one, two, three, or four heteroatoms selected from nitrogen, oxygen and sulfur, wherein not more than one of the heteroatoms is oxygen or sulfur;

$R^1$ is selected from —C(O)OR$^a$, —C(O)NR$^b$R$^c$, $C_{2-6}$alkenyl, $C_{1-6}$ alkyl, $C_{3-12}$cycloalkyl, and phenyl, wherein $C_{1-6}$alkyl is optionally substituted with one or two $R^3$, $C_{3-12}$cycloalkyl is optionally substituted with one or two halo or with —OR$^a$ or —NR$^b$R$^c$, and phenyl is optionally substituted with one or two halo or with —OR$^a$, NR$^b$R$^c$, or $C_{1-4}$alkyl, wherein $C_{1-4}$alkyl is optionally substituted with —OR$^a$;

$R^2$ is hydrogen or phenyl;

$R^3$ is selected from —C(O)OR$^a$, —C(O)NR$^d$R$^e$, —OR$^f$, —NR$^b$R$^g$, —CN, $C_{3-6}$cycloalkyl, phenyl, and naphthyl, wherein $C_{3-6}$cycloalkyl is optionally substituted with one or two halo or with —OR$^a$, and phenyl is optionally substituted with one or two halo or with —CN;

$R^a$, $R^b$, $R^c$, and $R^d$ are each independently hydrogen or $C_{1-3}$alkyl;

$R^e$ is hydrogen or $C_{1-3}$alkyl, optionally substituted with $C_{3-6}$cycloalkyl, —OR$^a$, phenyl, pyridyl, or 4-phenylpiperazinyl; or $R^d$ and $R^e$ taken together with the nitrogen atom to which they are attached form piperidinyl;

$R^f$ is hydrogen, $C_{1-3}$alkyl, or phenyl;

$R^g$ is hydrogen or $C_{1-3}$alkyl, optionally substituted with phenyl; and m is 0, 1, or 2;

provided that when m is 0, $R^2$ is H;

or a pharmaceutically-acceptable salt thereof.

2. The compound of claim 1 wherein $R^1$ is selected from $C_{1-6}$alkyl, $C_{3-6}$cycloalkyl, and phenyl, wherein $C_{1-6}$alkyl is optionally substituted with one or two $R^3$, $C_{3-6}$cycloalkyl is optionally substituted with one or two halo or with —OR$^a$ or —NR$^b$R$^c$, and phenyl is optionally substituted with one or two halo or with —OR$^a$, —NR$^b$R$^c$, or $C_{1-4}$alkyl, wherein $C_{1-4}$alkyl is optionally substituted with —OR$^a$.

3. The compound of claim 1 wherein $R^1$ is selected from $C_{1-6}$alkyl, cyclopentyl, cyclohexyl, and phenyl, wherein $C_{1-6}$alkyl is optionally substituted with one $R^3$, and cyclohexyl and phenyl are each optionally substituted with one or two fluoro.

4. The compound of claim 3 wherein $R^3$ is selected from —OR$^f$, $C_{3-6}$cycloalkyl, and phenyl, wherein $C_{3-6}$cycloalkyl is optionally substituted with one or two halo or with —OR$^a$, and phenyl is optionally substituted with one or two halo.

5. The compound of claim 4 wherein $R^3$ is selected from cyclopentyl, cyclohexyl, and phenyl, wherein cyclohexyl and phenyl are each optionally substituted with one or two fluoro.

6. The compound of claim 1 wherein A is selected from triazolenyl, imidazolenyl, oxadiazolenyl, tetrazolenyl, pyrrolenyl, furanenyl, and thiofuranenyl.

7. The compound of claim 1 wherein A is selected from triazolenyl, imidazolenyl, and oxadiazolenyl.

8. The compound of claim 7 wherein:

$R^1$ is selected from $C_{1-6}$alkyl, $C_{3-6}$cycloalkyl, and phenyl, wherein $C_{1-6}$alkyl is optionally substituted with one or two $R^3$, $C_{3-6}$cycloalkyl is optionally substituted with one or two halo or with —OR$^a$ or —NR$^b$R$^c$, and phenyl is optionally substituted with one or two halo or with —OR$^a$, NR$^b$R$^c$, or $C_{1-4}$alkyl, wherein $C_{1-4}$alkyl is optionally substituted with —OR$^a$;

R³ is selected from —OR^f, C₃₋₆cycloalkyl, and phenyl, wherein C₃₋₆cycloalkyl is optionally substituted with one or two halo or with —OR^a, and phenyl is optionally substituted with one or two halo; and
R^f is hydrogen.

9. The compound of claim 1 wherein R¹-A- is selected from a moiety of formula (a), (b), (c), (d) and (e):

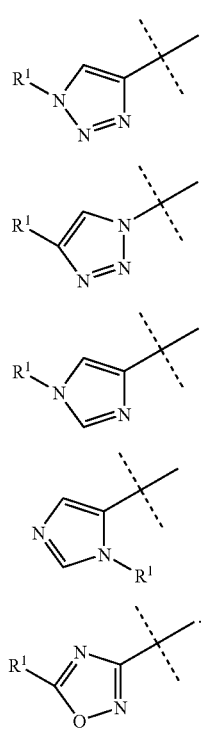

10. The compound of claim 9 wherein the compound is a compound of formula (Ia):

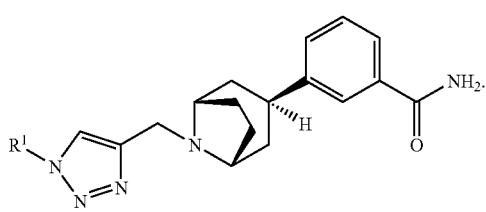

11. The compound of claim 9 wherein the compound is a compound of formula (Ib):

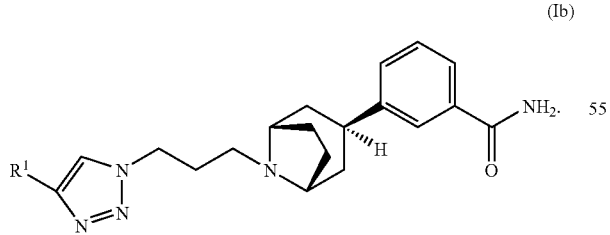

12. The compound of claim 1 wherein the compound is selected from:
3-endo-[8-(1-cyclohexyl-1H-[1,2,3]triazol-4-ylmethyl)-8-azabicyclo[3.2.1]oct-3-yl]benzamide;
3-endo-{8-[1-(4,4-difluorocyclohexyl)-1H-1,2,3-triazol-4-ylmethyl]-8-azabicyclo[3.2.1]oct-3-yl}benzamide;
3-endo-(8-{3-[4-(2,4-difluorophenyl)-[1,2,3]triazol-1-yl]-propyl}-8-azabicyclo[3.2.1]oct-3-yl)benzamide;
3-endo-{8-[1-(2-ethylbutyl)-1H-[1,2,3]triazol-4-ylmethyl]-8-aza-bicyclo[3.2.1]oct-3-yl}benzamide; and
3-endo-(8-{2-[4-(2,4-difluorophenyl)-[1,2,3]triazol-1-yl]ethyl}-8-aza-bicyclo[3.2.1]oct-3-yl)benzamide;
and pharmaceutically-acceptable salts thereof.

13. A pharmaceutical composition comprising the compound of claim 1 and a pharmaceutically-acceptable carrier.

14. A process for preparing a compound of formula (I),

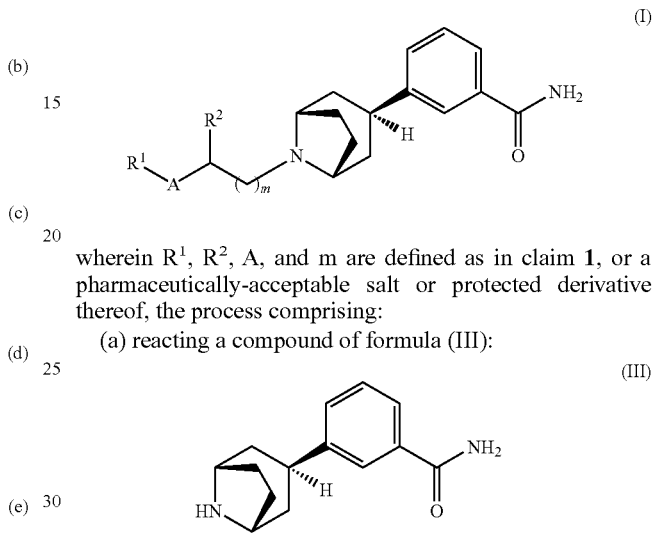

wherein R¹, R², A, and m are defined as in claim 1, or a pharmaceutically-acceptable salt or protected derivative thereof, the process comprising:
(a) reacting a compound of formula (III):

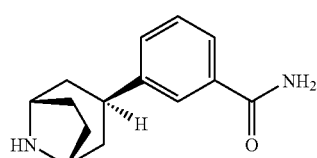

with a compound of formula (IV):

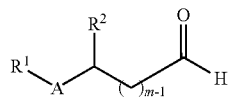

or
(b) wherein A is bonded to R¹ via a nitrogen atom on A,
(i) reacting a compound of formula (III) with a compound of formula (V)

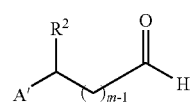

wherein A' is A or a protected form of A, and, optionally deprotecting the product of the reaction, to provide a compound of formula (VI):

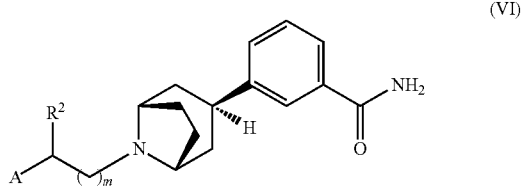

and
(ii) reacting a compound of formula (VI) with a compound of the formula R¹—X, wherein X is a leaving group, to provide a compound of formula (I) or a salt or protected derivative thereof.

15. A process for preparing a compound of formula (Ia):

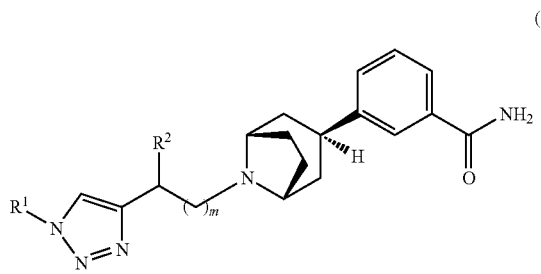
(Ia)

or a salt or protected derivative thereof, wherein $R^1$, $R^2$ and m are defined as in claim 1, the process comprising reacting a compound of formula (VII):

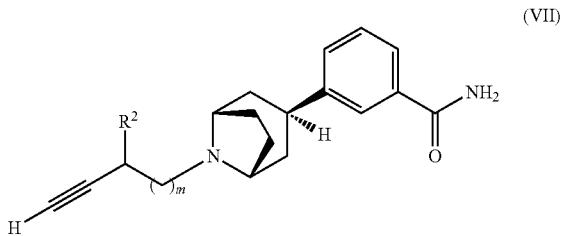
(VII)

with a compound of the formula $R^1$—$N_3$ to provide a compound of formula (Ia) or a salt or protected derivative thereof.

16. The process of claim 15 wherein the reaction is performed in the presence of a copper catalyst.

17. A process for preparing a compound of formula (Ib):

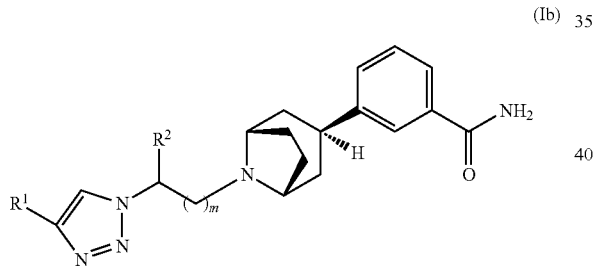
(Ib)

or a salt or protected derivative thereof, wherein $R^1$ and $R^2$ are defined as in claim 1 and m is 1 or 2, the process comprising reacting a compound of formula (VIII):

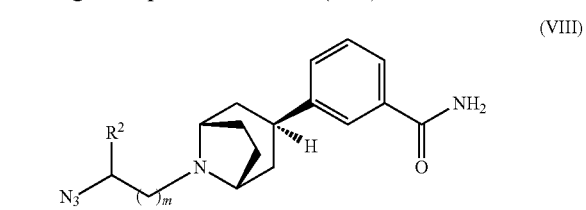
(VIII)

with a compound of the formula $R^1C \equiv CH$ to provide a compound of formula (Ib) or a salt or protected derivative thereof.

18. The process of claim 17 wherein the reaction is performed in the presence of a copper catalyst.

19. A compound of formula (VII):

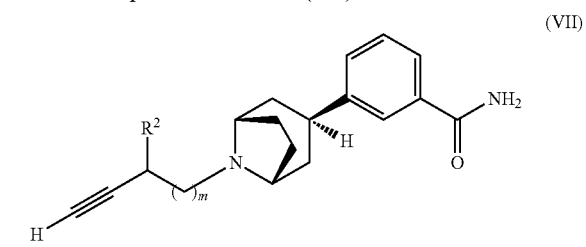
(VII)

wherein $R^2$ is hydrogen or phenyl and m is 0, 1, or 2;

or a compound of formula (VIII):

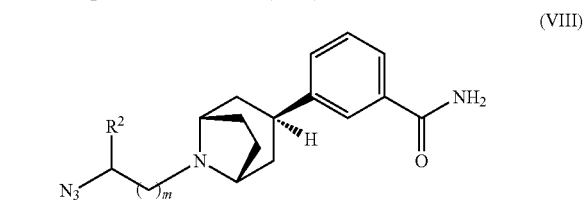
(VIII)

wherein $R^2$ is hydrogen or phenyl and m is 1 or 2.

* * * * *